US012703737B2

(12) United States Patent
Scheper et al.

(10) Patent No.: US 12,703,737 B2
(45) Date of Patent: Aug. 11, 2026

(54) RECOMBINANT PROTEINS BASED ON FIBRINOGEN

(71) Applicant: Sartorius Lab Instruments GmbH & Co. KG, Göttingen (DE)

(72) Inventors: Thomas Scheper, Hannover (DE); Iliyana Pepelanova, Hannover (DE); Pia Gellermann, Hannover (DE); Sabrina Grünert, Marklohe (DE)

(73) Assignee: Sartorius Lab Instruments GmbH & Co. KG, Göttingen (DE)

( * ) Notice: Subject to any disclaimer, the term of this patent is extended or adjusted under 35 U.S.C. 154(b) by 734 days.

(21) Appl. No.: 17/925,551

(22) PCT Filed: May 20, 2021

(86) PCT No.: PCT/EP2021/063524
§ 371 (c)(1),
(2) Date: Nov. 15, 2022

(87) PCT Pub. No.: WO2021/239584
PCT Pub. Date: Dec. 2, 2021

(65) Prior Publication Data

US 2024/0294607 A1 Sep. 5, 2024

(30) Foreign Application Priority Data

May 26, 2020 (EP) .................................... 20176426

(51) Int. Cl.
*C07K 14/75* (2006.01)
*C12N 15/70* (2006.01)
*A61K 38/00* (2006.01)

(52) U.S. Cl.
CPC .............. *C07K 14/75* (2013.01); *C12N 15/70* (2013.01); *A61K 38/00* (2013.01); *C07K 2319/21* (2013.01)

(58) Field of Classification Search
CPC ........................... C07K 14/75; C07K 2319/21; C07K 2319/40; C12N 15/70; A61K 38/00; B33Y 70/00; B33Y 80/00
See application file for complete search history.

(56) References Cited

U.S. PATENT DOCUMENTS

2009/0324590 A1* 12/2009 Kambadur .............. A61P 31/18
435/69.7

FOREIGN PATENT DOCUMENTS

| | | | | |
|---|---|---|---|---|
| EP | 2239267 | A1 | 10/2010 | |
| EP | 2963059 | A1 | 1/2016 | |
| WO | WO-2014115087 | A2 * | 7/2014 | ............. C07K 14/75 |
| WO | 2014115087 | A3 | 10/2014 | |

OTHER PUBLICATIONS

Gaberc-Porekar (Chem.Eng. Technol., 2005, 28, No. 11, 1306-1314). (Year: 2005).*
Anonymous , "Fibrinogen gamma Chain (FGG) (AA 27-453) protein (His tag) 1 Image Overview Protein Name: Fibrinogen gamma Chain (FGG)", URL:https://www.antibodies-online.com/productsheets/ABIN3092604.pdf, 5 pages (2020).
Bolyard, M , et al., "High-level expression of a functional human fibrinogen gamma chain in *Escherichia coli*", Gene 66, 183-192 (1988).
Patent Cooperation Treaty , International Searching Authority for PCT/EP2021/063524, 5 pages, dated Aug. 27, 2021.
Zeh, N , et al., "Exploring synthetic biology for the development of a sensor cell line for automated bioprocess control", Scientific Reports 12 (2268), 11 pages (2022).

* cited by examiner

*Primary Examiner* — Sudhakar Katakam
(74) *Attorney, Agent, or Firm* — Viksnins Harris Padys Malen LLP

(57) ABSTRACT

The present invention relates to isolated, recombinant polypeptides comprising the gamma chain of fibrinogen and a His-Tag. The present invention further relates to nucleic acids encoding said polypeptides, vectors comprising said nucleic acids, host cells, preferably bacterial host cells, comprising said nucleic acids or vectors, biohybrid materials comprising conjugates comprising said polypeptides, uses of the above, and methods for producing said polypeptides.

15 Claims, 11 Drawing Sheets

Figure 1:
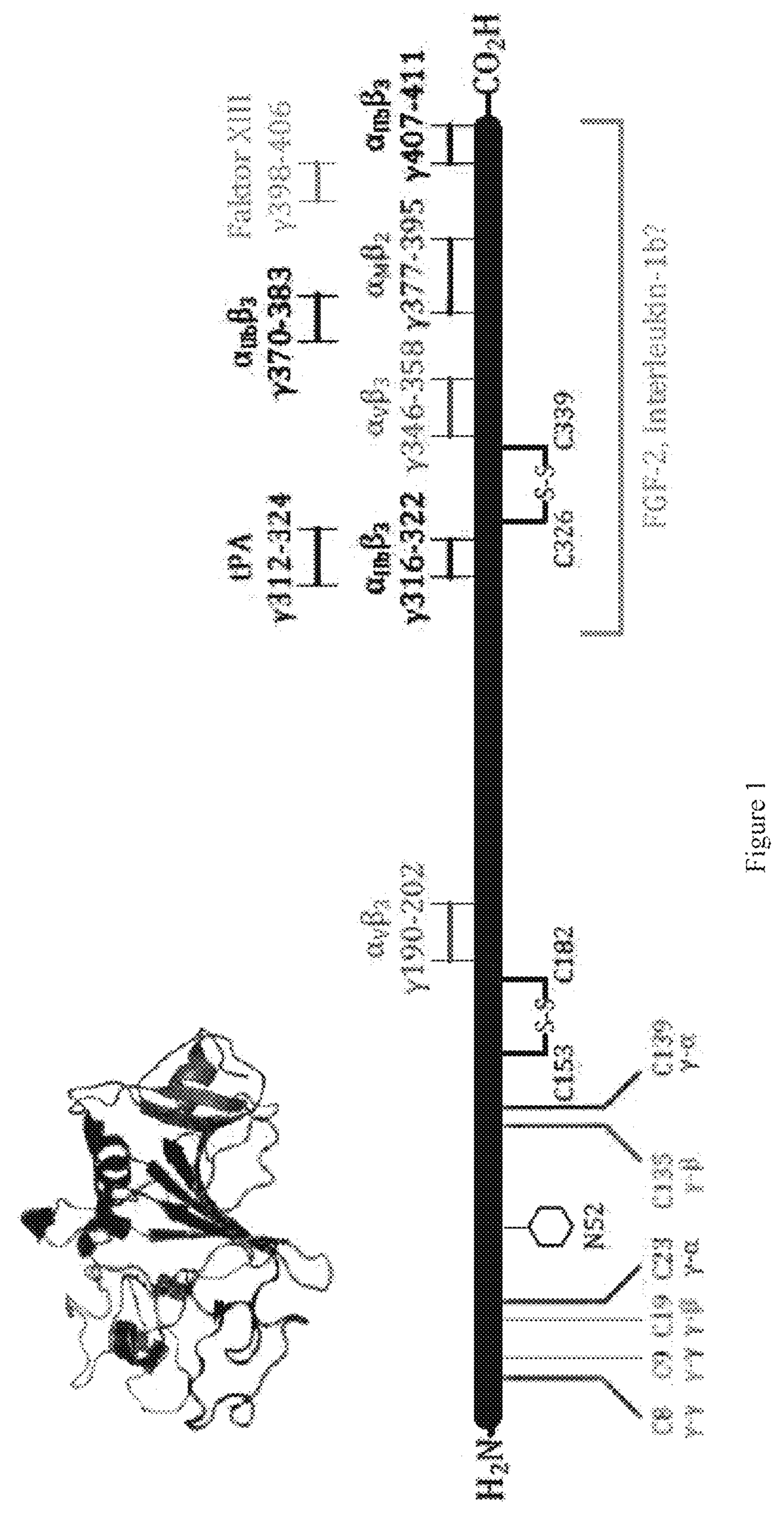

Specification includes a Sequence Listing.

Step 1 = IMAC sample application
wash
elution
1.
300
250
200
150
100
50
0
$A_{280}$ (AU)
0
10
20
30
40
Volume (mL)

Figure 3

RECOMBINANT PROTEINS BASED ON FIBRINOGEN

CROSS-REFERENCE TO RELATED APPLICATION(S)

This application claims the benefit of priority of EP Application Serial No. 20176426.3 filed May 26, 2020.

The present invention relates to isolated, recombinant polypeptides comprising the gamma chain of fibrinogen and a His-Tag. The present invention further relates to nucleic acids encoding said polypeptides, vectors comprising said nucleic acids, host cells, preferably bacterial host cells, comprising said nucleic acids or vectors, biohybrid materials comprising conjugates comprising said polypeptides, uses of the above, and methods for producing said polypeptides.

Proteins from the extracellular matrix (ECM) are frequently used in cell culture applications and are valued for their ability to provide cells with key biochemical factors, necessary for their cell attachment, growth and proliferation. The blood protein fibrinogen is a precursor to fibrin and plays an important role in wound healing, hemostasis and angiogenesis. After formation of the blood clot, fibrin serves as a new provisional ECM for tissue regeneration. Fibrinogen is a hexamer composed of a double set of alpha, beta and gamma chains, connected to each other via intra- and interchain disulfide bridges. The natural polymerization of fibrinogen to fibrin is a multi-step enzymatic process catalyzed by thrombin following vascular injury. Thrombin cleaves two short amino acid sequences in the amino-termini of the Aα and Bβ chain of the fibrin precursor fibrinogen. As a consequence, polymerization sites within the fibrin molecule are exposed, which leads to the polymerization of single fibrinogen molecules to a 3D fibrin network. Further stabilization of this network is achieved by covalent cross-linking of the gamma chains which is catalyzed by factor XIIIa.

The most widespread medical use of fibrin is as a hemostatic agent and tissue sealant. The first fibrin glue on the market which was FDA-approved was Tisseel® from Baxter, but many other products have followed since then. These formulations are acting as hemostats, sealants and tissue adhesives in different clinical settings. They are all produced from homologous fibrinogen and thrombin from pooled blood donations. Since fibrin for biomedical and cell culture applications is sourced from human or animal blood, there is always a residual risk of pathogenic transmission. In addition, the material is subjected to a natural batch-to-batch variation due to its sourcing, which makes fibrin materials difficult to standardize for biomedical research. These variations may hinder GMP (good manufacturing practice) requirements for a specific, newly developed fibrin-based products.

A more secure way to obtain pure proteins of consistent quality and free of the risk of pathogenic transmission is recombinant production. Most heterologous expression systems for production of the complete fibrinogen molecule are based on mammalian cells due to the complex structure and post-translational modifications involved. Accordingly, recombinant fibrinogen has been expressed in baby hamster cells, mainly with the purpose of studying its subunit interactions and assembly. Further, fully-assembled fibrinogen has been produced in the PER.C6® cell line. CHO cells have also been used for recombinant fibrinogen production and yields have been somewhat improved throughout the years. Another approach to obtain fully-assembled fibrinogen is to produce it in the milk of transgenic animals. This has been demonstrated for example in dairy cows and mice.

Applications of fibrinogen are all based on the attractive properties of the material, especially its propensity to bind growth factors, as well as its interaction with platelets, leucocytes, fibroblasts and endothelial cells. Fibrinogen is therefore a widely used biopolymer in tissue engineering for the repair of damaged tissues/organs, in cell culture as coating or 3D matrix, but also as a cell and drug delivery agent, especially for growth factor delivery. Fibrinogen binds multiple growth factors with well-investigated affinity, especially fibroblast growth factor 2 (FGF-2) and vascular endothelial growth factor (VEGF), as well as heparin. The latter has been used as a linker to growth factors, which do not naturally bind to fibrin (nerve growth factor (NGF), neutrophin-3). Such growth factor-immobilized constructs can be used to deliver growth factors for therapeutic or cell culture applications. For example, in the area of cell culture coatings, fibrin has been used with great success for solid growth factor delivery, increasing survival and proliferation of MG-63 cells in contact with FGF-2 patterns, which were immobilized by the native affinity of fibrin for this growth factor. There are numerous reports that FGF-2 binding to fibrinogen or fibrin protects the growth factor from degradation, increasing its long-term effects in cell culture. It also seems that the fibrinogen-FGF-2 pair enhances the proliferative capacity of the growth factor, compared to fibrinogen or FGF-2 alone.

Fibrinogen possesses multiple RGD, AGDV (SEQ ID NO: 7) and integrin binding sites, which allow it to interact with various types of cells. This bioactivity makes it an attractive matrix for stem cell differentiation, cell delivery/cell enrichment and tissue engineering. In cell culture application, fibrinogen coatings have been shown to be a viable alternative to laminin (Geltrex), in the culturing of induced pluripotent stem cells (iPSCs). iPSCs cultured on fibrinogen coatings retained their pluripotency and ability to differentiate into different germinal layers. As such, fibrinogen represents an interesting regulatory-compliant material for developing cell therapy applications. Another interesting application in the area of cell isolation/enrichment is using insoluble fibrinogen particles to create a cell-affinity column, which can be used to harvest and grow mesenchymal cells (fibroblasts, endothelial cells) from various tissues such as bone marrow without using trypsinization. This technology can also be used for trapping cancer cells from blood suspensions.

Despite their interesting bioactivity, fibrinogen-based materials frequently suffer from poor mechanical properties and rapid degradation. This sometimes necessitates the need to modify the material with synthetic polymers to create biohybrid materials of superior characteristics. These semi-synthetic materials combine the inherent bioactivity of fibrinogen with tailor-made, tunable properties coming from the synthetic moiety.

PEG is an attractive polymer for modification, because it is biologically inert and can be used to precisely tune mechanical properties by controlling chain length and degree of crosslinking. Amine-reactive PEG has been conjugated to fibrinogen yielding hydrogels for 3D cell culture which could be loaded with growth factors (PDGF, TGF-β) and supported MSC viability and neovascularization. A different approach has been used by creating PEGylated precursors by crosslinking denatured fibrinogen to PEG-DA. Photopolymerization of these PEGylated precursors leads to scaffolds which enable migration, cell spreading and controllable proteolytic degradation. Another promising approach in research are thermo-sensitive hydrogels based on fibrin in combination with the Pluronic® F127 copolymer. Pluronic® F127 copolymer undergoes reverse thermal gelation in response to temperature changes. The conjugation of fibrinogen to Pluronic® F127 enables the control over physical properties while retaining full cell compatibility of the hybrid hydrogel.

A recombinant fibrinogen-based material could represent a cost-efficient and regulatory compliant sourcing of fibrinogen, which opens the door to multiple cell culture and biomedical applications, as described above.

Accordingly, the technical problem underlying the present invention is the provision of a fibrinogen-like material that can be recombinantly produced in a fast, easy and cost-effective manner while at the same time avoiding the use of human or animal blood, as well as the use of mammalian cell culture, and respective means of producing such material.

The solution to the above technical problem is achieved by the embodiments characterized in the claims.

In particular, in a first aspect, the present invention relates to an isolated, recombinant polypeptide, comprising (i) the gamma chain of fibrinogen, and (ii) a His-Tag.

As used herein, the term "recombinant polypeptide" refers to an artificially produced polypeptide, i.e., a polypeptide that results from the expression of a recombinant, i.e., artificially produced, DNA in a living cell.

The isolated, recombinant polypeptide of the present invention comprises a gamma chain of fibrinogen, preferably a gamma chain of human fibrinogen. In preferred embodiments, said gamma chain of fibrinogen comprises binding sites for integrins, leukocytes, platelets, fibroblasts, endothelial cells and/or fibroblast growth factor 2 (FGF-2). Specifically, said gamma chain of fibrinogen can comprise one or more or all of the following specific binding sites:

- Platelet binding site: γC-dodecapeptide for binding integrin $\alpha_{IIb}\beta_3$ (HHLGGAKQAGDV; SEQ ID NO: 8) on $FGG_{427-438}$
- Leucocyte, neutrophil, monocyte integrin Mac-1 or $\alpha_M\beta_2$ binding site at $FGG_{404-422}$ (YSMKKTTMKIIPFNRLTIG; SEQ ID NO: 9)
- Binding sites for integrin $\alpha_V\beta_3$ leading to binding of endothelial, fibroblasts and tumor cells at $FGG_{217-229}$ (WTVFQKRLDGSV; SEQ ID NO: 10) and $FGG_{373-385}$ (GVYYQGGTYSKAS; SEQ ID NO: 11)
- C-terminal region FGG: growth factors FGF-2 and interleukin-β binding site
- Factor XIII crosslinking site, EGG Lysine at 433 and FGG Glutamine at 425/426

More preferably, said gamma chain of fibrinogen comprises or consists of (i) the amino acid sequence according to SEQ ID NO: 1, or (ii) an amino acid sequence having at least 80%, at least 81%, at least 82%, at least 83%, at least 84%, at least 85%, at least 86%, at least 87%, at least 88%, at least 89%, at least 90%, at least 90.5%, at least 91%, at least 91.5%, at least 92%, at least 92.5%, at least 93%, at least 93.5%, at least 94%, at least 94.5%, at least 95%, at least 95.25%, at least 95.5%, at least 95.75%, at least 96%, at least 96.25%, at least 96.5%, at least 96.75%, at least 97%, at least 97.25%, at least 97.5%, at least 97.75%, at least 98%, at least 98.1%, at least 98.2%, at least 98.3%, at least 98.4%, at least 98.5%, at least 98.6%, at least 98.7%, at least 98.8%, at least 98.9%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 1 and having fibrinogen gamma chain activity. In this context, the term "having fibrinogen gamma chain activity" refers to the characteristic of having functional binding sites for integrins, leukocytes, platelets, fibroblasts, endothelial cells and/or FGF-2.

Further, the recombinant polypeptide of the present invention comprises a His-Tag, i.e., a polyhistidine-tag comprising an amino acid motif comprising at least six histidine (His) residues. Preferably, said His-Tag comprises or consists of (i) the amino acid sequence according to SEQ ID NO: 2, or (ii) an amino acid sequence having at least 80%, at least 81%, at least 82%, at least 83%, at least 84%, at least 85%, at least 86%, at least 87%, at least 88%, at least 89%, at least 90%, at least 90.5%, at least 91%, at least 91.5%, at least 92%, at least 92.5%, at least 93%, at least 93.5%, at least 94%, at least 94.5%, at least 95%, at least 95.25%, at least 95.5%, at least 95.75%, at least 96%, at least 96.25%, at least 96.5%, at least 96.75%, at least 97%, at least 97.25%, at least 97.5%, at least 97.75%, at least 98%, at least 98.1%, at least 98.2%, at least 98.3%, at least 98.4%, at least 98.5%, at least 98.6%, at least 98.7%, at least 98.8%, at least 98.9%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 2 and having His-Tag functionality. In this context, the term "having His-Tag functionality" refers to the characteristic of having an amino acid motif comprising at least six, preferably consecutive, histidine (His) residues.

In preferred embodiments, the isolated, recombinant polypeptide of the present invention comprises (i) the amino acid sequence according to SEQ ID NO: 3, or (ii) an amino acid sequence having at least 80%, at least 81%, at least 82%, at least 83%, at least 84%, at least 85%, at least 86%, at least 87%, at least 88%, at least 89%, at least 90%, at least 90.5%, at least 91%, at least 91.5%, at least 92%, at least 92.5%, at least 93%, at least 93.5%, at least 94%, at least 94.5%, at least 95%, at least 95.25%, at least 95.5%, at least 95.75%, at least 96%, at least 96.25%, at least 96.5%, at least 96.75%, at least 97%, at least 97.25%, at least 97.5%, at least 97.75%, at least 98%, at least 98.1%, at least 98.2%, at least 98.3%, at least 98.4%, at least 98.5%, at least 98.6%, at least 98.7%, at least 98.8%, at least 98.9%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 3 and having fibrinogen activity and His-Tag functionality. In this context, a protein consisting of the amino acid sequence according to SEQ ID NO: 3 has an amino acid composition of 13.01% acidic amino acids, 34.47% neutral amino acids, 15.3% basic amino acids, and 37.21% hydrophobic amino acids, a molecular weight of 49.7 and a pl of 5.95. Further, the amino acid sequence according to SEQ ID NO: 3 comprises a factor Xa protease cleavage site allowing for removal of the His-Tag from the EGG if desired.

In specific embodiments, the isolated, recombinant polypeptide of the present invention is expressed in a bacterial host cell, preferably in an *Escherichia coli* (*E. coli*) host cell.

In a second aspect, the present invention relates to an isolated nucleic acid, preferably a DNA, encoding the polypeptide according to the first aspect of the present invention.

In preferred embodiments, the isolated nucleic acid of the present invention comprises (i) the nucleotide sequence according to SEQ ID NO: 4, or (ii) a nucleotide sequence having at least 80%, at least 81%, at least 82%, at least 83%, at least 84%, at least 85%, at least 86%, at least 87%, at least 88%, at least 89%, at least 90%, at least 90.5%, at least 91%, at least 91.5%, at least 92%, at least 92.5%, at least 93%, at least 93.5%, at least 94%, at least 94.5%, at least 95%, at least 95.25%, at least 95.5%, at least 95.75%, at least 96%, at least 96.25%, at least 96.5%, at least 96.75%, at least 97%, at least 97.25%, at least 97.5%, at least 97.75%, at least 98%, at least 98.1%, at least 98.2%, at least 98.3%, at least 98.4%, at least 98.5%, at least 98.6%, at least 98.7%, at least 98.8%, at least 98.9%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 4 and encoding a polypeptide having fibrinogen activity, or (iii) a nucleotide sequence that is complementary to a nucleotide sequence under (i) or (ii).

In further preferred embodiments, the isolated nucleic acid of the present invention comprises (i) the nucleotide sequence according to SEQ ID NO: 6, or (ii) a nucleotide sequence having at least 80%, at least 81%, at least 82%, at least 83%, at least 84%, at least 85%, at least 86%, at least 87%, at least 88%, at least 89%, at least 90%, at least 90.5%, at least 91%, at least 91.5%, at least 92%, at least 92.5%, at least 93%, at least 93.5%, at least 94%, at least 94.5%, at least 95%, at least 95.25%, at least 95.5%, at least 95.75%, at least 96%, at least 96.25%, at least 96.5%, at least 96.75%, at least 97%, at least 97.25%, at least 97.5%, at least 97.75%, at least 98%, at least 98.1%, at least 98.2%, at least 98.3%, at least 98.4%, at least 98.5%, at least 98.6%, at least 98.7%, at least 98.8%, at least 98.9%, at least 99%, at least 99.1%, at least 99.2%, at least 99.3%, at least 99.4%, at least 99.5%, at least 99.6%, at least 99.7%, at least 99.8%, or at least 99.9% sequence identity to SEQ ID NO: 6 and encoding a polypeptide having fibrinogen activity and His-Tag functionality, or (iii) a nucleotide sequence that is complementary to a nucleotide sequence under (i) or (ii).

The nucleic acid of the present invention may further comprise suitable up- and downstream regulatory sequences, including promoter sequences, enhancer sequences, stop codons, and others as known in the art.

In a third aspect, the present invention relates to a vector comprising the nucleic acid of the present invention. In this context, the term "vector" encompasses plasmid vectors, cosmid vectors, viral vectors, and artificial chromosomes, as known in the art. In particular embodiments, the vector is a plasmid vector, e.g. an expression vector suitable for protein expression in bacterial host cells, in particular in *E. coli* host cells. Respective vectors are known in the art.

In a fourth aspect, the present invention relates to a host cell comprising the nucleic acid of the present invention or the vector of the present invention. In preferred embodiments, said host cell is a bacterial host cell, more preferably an *E. coli* host cell. In this context, the term "*E. coli* host cell" encompasses any suitable *E. coli* strains known in the art.

In a fifth aspect, the present invention relates to a biohybrid material, comprising a conjugate comprising the polypeptide of the present invention and one or more moieties, selected from the group consisting of polyethylene glycol (PEG), PEG derivatives (such as PEG diacrylate (PEG-DA) and poly(oligo(ethylene glycol) methyl ether methacrylate (POEGMA)), poly(N-(2-hydroxypropyl)-methacrylamide) (PHPMA) and HPMA copolymers, poly(vinylpyrrolidone) (PVP), poly(ethyleneimine) (PEI), poly(acroloylmorpholine) (PAcM), poly(2-ethyl 2-oxazoline) (PEOZ), divinylethermaleic anhydride/acid copolymer (DIVEMA), poly(styrene-co-maleic acid/anhydride) (SMA), poly(vinyl alcohol) (PVA) and temperature-sensitive polymers including poloxamers (Pluronic), poly(N-isopropylacrylamide) (PNIPAM), poly(N, N-diethylacrylamide) (PDEAM), poly(methylvinylether) (PMVE), poly(N-vinylcaprolactam) (PNVCI), and mixtures thereof. In this context, the term "poloxamer" refers to non-ionic triblock copolymers composed of a central hydrophobic chain of polyoxypropylene (poly(propylene oxide)) flanked by two hydrophilic chains of polyoxyethylene (poly(ethylene oxide)). In specific embodiments, the poloxamer is the compound known under the trade name Pluronic® F-127, i.e., a polyoxyethylene-polyoxypropylene block copolymer having the molecular formula $EO_{100}PO_{65}EO_{100}$, CAS Number 9003-11-6, as known in the art.

As used herein, the term "conjugate" refers to the fact that the polypeptide of the present invention and the above one or more moieties are covalently bound to each other.

In a sixth aspect, the present invention relates to in vitro uses of the polypeptide or biohybrid material of the present invention, i.e., uses that are not performed on the human or animal body. Specifically, the present invention relates to the use of the isolated, recombinant polypeptide of the present invention or the biohybrid material of the present invention as a cell culture plate coating, as a 3D cell culture matrix, as an in vitro tissue/organ model, in vitro drug testing platform, as an in vitro cell and/or drug delivery platform, as a coating for cell enrichment and/or isolation, as a coating for growth factor (FGF-2) enrichment and/or isolation, as bioink for bioprinting, or in enzyme-free cell detachment.

In a related seventh aspect, the present invention relates to the recombinant polypeptide of the present invention or the biohybrid material of the present invention for use in applications that are performed on the human or animal body, i.e., for use in wound healing, in vivo tissue engineering, in vivo tissue/organ repair, or in vivo cell and/or drug delivery.

In an eighth aspect, the present invention relates to a method for the production of the polypeptide of the present invention, comprising the steps of (a) providing a host cell of the present invention,
(b) culturing said host cell under conditions that allow expression of said polypeptide, and
(c) isolating said polypeptide from said host cells and/or the culture medium.

In this aspect, the host cell is preferably a bacterial host cell, more preferably an *E. coli* host cell.

Means for culturing said host cell under conditions that allow expression of said polypeptide, as well as means for isolating said polypeptide from said host cells and/or the culture medium, are not particularly limited and are known in the art.

In the present invention, a partial sequence of human fibrinogen was produced, consisting of the fibrinogen gamma chain (EGG) and a His-tag for purification, in *E. coli*. Moreover, it was shown that FGG's performance as a cell culture plate coating is indistinguishable to human fibrinogen. It was also shown that modification with a synthetic polymer results in a biohybrid material, FGG-PEG, which is photoactive and can be crosslinked by light. Both forms of the material, the basic biopolymer FGG and its biohybrid forms can be used in a variety of cell culture and lab solution applications.

The biological properties of FGG are derived from its parent molecule, fibrinogen. Fibrinogen is a blood protein and precursor to fibrin which serves physiologically as (a) provisional cell matrix, (b) possesses hemostatic properties (wound healing applications), (c) enhances stem cell differentiation/delivery and (d) performs angiogenesis induction. EGG consists of the total mature protein sequence of the fibrinogen gamma chain plus a His-tag and contains binding sites for integrins, leukocytes, platelets, fibroblasts, endothelial cells and fibroblast growth factor 2 (FGF-2).

Fibrinogen is widely used in biomedical applications (especially as a tissue sealant) and is usually derived from blood. While blood represents a widely available resource, there are several disadvantages related to its use. In particular, there is always a residual risk of pathogenic transmission and there is considerable batch-to-batch variability of the resulting fibrinogen material. To address these drawbacks, the present invention provides a recombinant, partial fibrinogen sequence produced in *E. coli*. The advantage of using a simple host microorganism, as opposed to mammalian cell culture, is virus-free sourcing and a more cost-efficient production. Indeed, the vast majority of recombinant human fibrinogen is produced in mammalian cell lines. The advantages of the recombinant human FGG from *E. coli* include (i) virus-free production, (ii) cost-effective production by microbial fermentation in large amounts, (iii) uniform properties (e.g. as far as molecular weight (MW) and/or pl are concerned), and (iv) defined structure for further chemical modification if required.

Of note, the isolated, recombinant polypeptides of the present invention surprisingly and advantageously adopt a functionally active conformation, e.g. as far as active binding sites for integrins, leukocytes, platelets, fibroblasts, endothelial cells and FGF-2 are concerned, in a spontaneous manner, e.g. after a buffer change from a buffer containing high amounts of chaotropic agents (such as, e.g. 5M urea), or even directly out of a respective solution containing high amounts of chaotropic agents. In addition, inclusion bodies (IBs) of the polypeptides can even be used directly, e.g. to coat plates, without solubilization at all. This is even more surprising since the fibrinogen gamma chain on its own, i.e., in the absence of the other fibrinogen chains (alpha and beta chains), does not have a natural conformation. Nevertheless, the polypeptides of the present invention spontaneously adopt a conformation in which they are indistinguishable from native fibrinogen, e.g. when used as a cell culture plate coating. Accordingly, there is no need for any complex and time-consuming refolding procedures with the polypeptides of the present invention. Moreover, the advantage that it isn't necessary to perform chromatographic separation/isolation makes the product even more cost-efficient.

It has been shown that when used as a cell culture coating, the performance of FGG is indistinguishable from native fibrinogen. The main application of FGG is as a cell plate coating for mammalian cell culture. This can be further distinguished from other coatings by its propensity to bind and stabilize FGF-2 (solid growth factor delivery) and many types of specific cells. In its form as insoluble inclusion body, FGG can be used as a biodegradable matrix for harvesting anchorage-dependent cells from tissues or blood. Also, it can be used in this form for modification of disposable bags or chromatographic membranes, all with the purpose of providing a specific cell and growth factor affinity surface.

Advantages of the basic material FGG according to the present invention to existing solutions are all related to not having to use homologous fibrinogen from human or animal blood, i.e., having a certifiable material with reproducible material properties and no risk of pathogenic transmission. Additional advantages arise from the fact that the production is not performed in mammalian cell culture, but in *E. coli*, thus providing an animal component-free process, virus-free production and considerable cost-efficiency.

In order to increase the spectrum of FGG application according to the present invention, it is also possible to modify the basic material to create biohybrid materials which provide additional functionalities. These biohybrid EGG biopolymers can be used in 3D mammalian cell culture, or even more specifically, as photoactive bioinks in bioprinting or as temperature-responsive materials in the area of enzyme-free cell detachment.

Advantages of such modified biohybrid materials according to the present invention to existing solutions are again related to sourcing of the biological component FGG from recombinant technology and not from natural sources. A modified biohybrid material will thus have more reproducible mechanical and biological properties. Further, creating biohybrids from recombinant fibrinogen produced in mammalian cell culture will be surely prohibited by the high cost.

THE FIGURES SHOW

FIG. 1: Sequence of FGG showing binding sites of interest, disulfide bonds and connections to other chains as well as a 3D FGG structure model.

Figure 2:
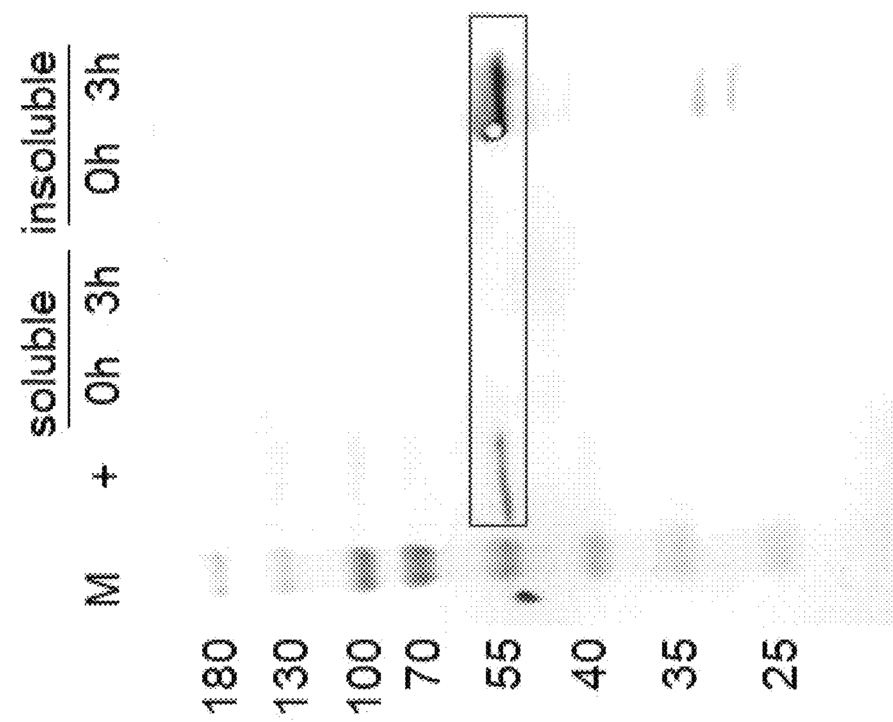
Figure 2:
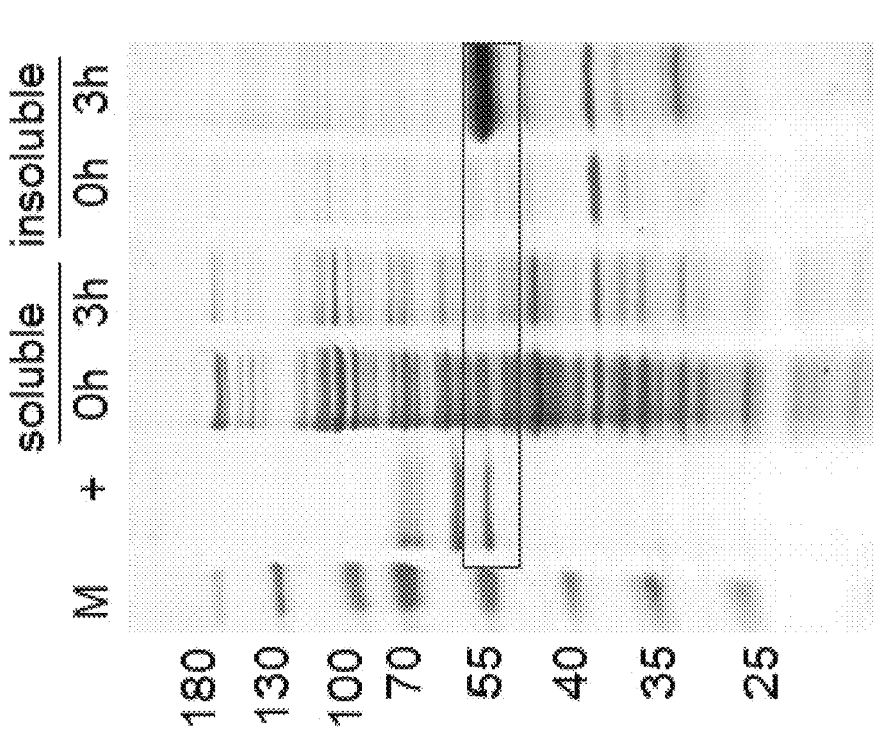

FIG. 2: SDS PAGE (A) and Western Blot (B) of soluble and insoluble fraction of cell lysates after 0 and 3 hours after induction with IPTG, M: molecular weight marker (in kDa), +: positive control as fibrinogen from human plasma, red box highlights position of gamma chain.

Figure 3:
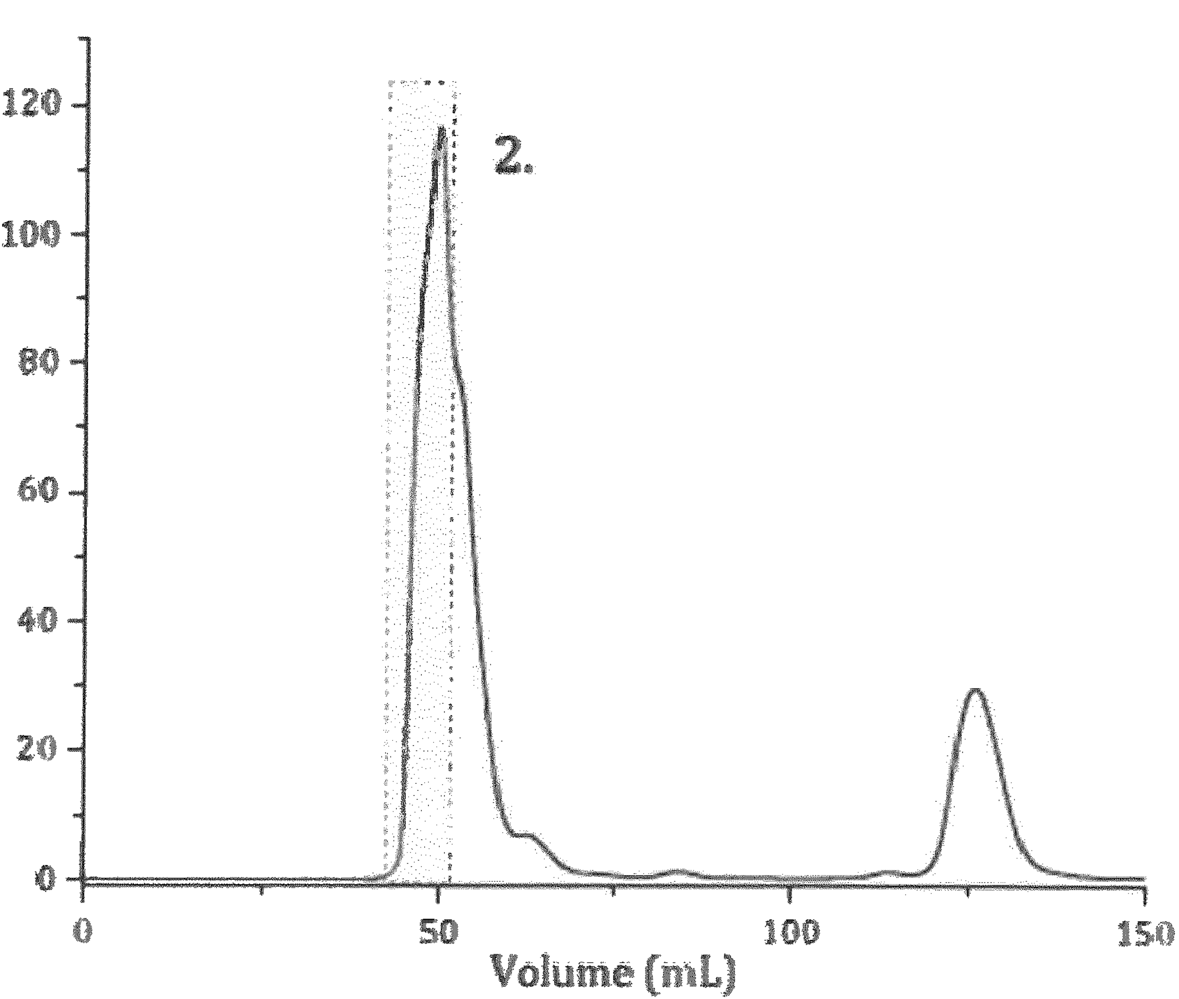
Figure 3:
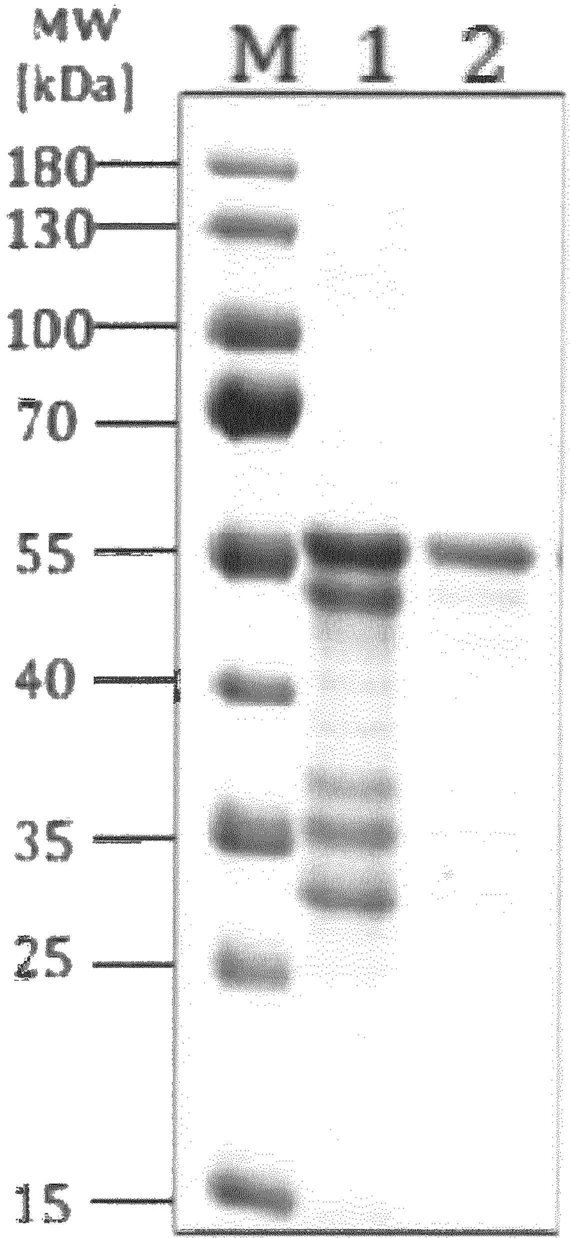

FIG. 3: Overview of the purification procedure. Two-step purification can be used to purify FGG. Step 1: Chromatogram of the solubilized inclusion bodies run on an IMAC column (HisTrap, 5 mL, GE Healthcare). The grey field indicates the sharp elution peak containing the tagged FGG Protein. Step 2: The peak eluted from the affinity column is subjected to size exclusion chromatography (SEC, Superdex 75 pg, GE Healthcare), which results in the separation of a peak, highlighted with grey. Further analysis of peaks via SDS-PAGE reveals the isolation of FGG at ca. 55 kDa.

Figure 4A:
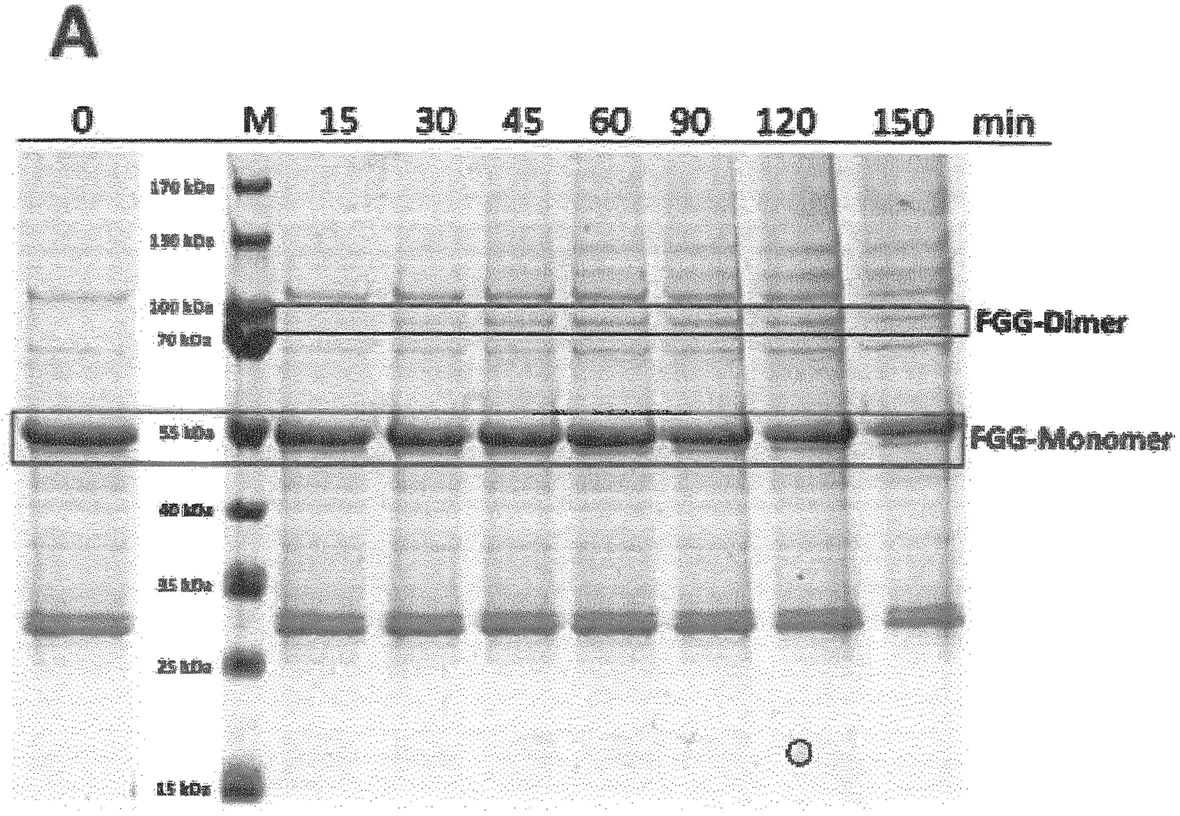
Figure 4B:
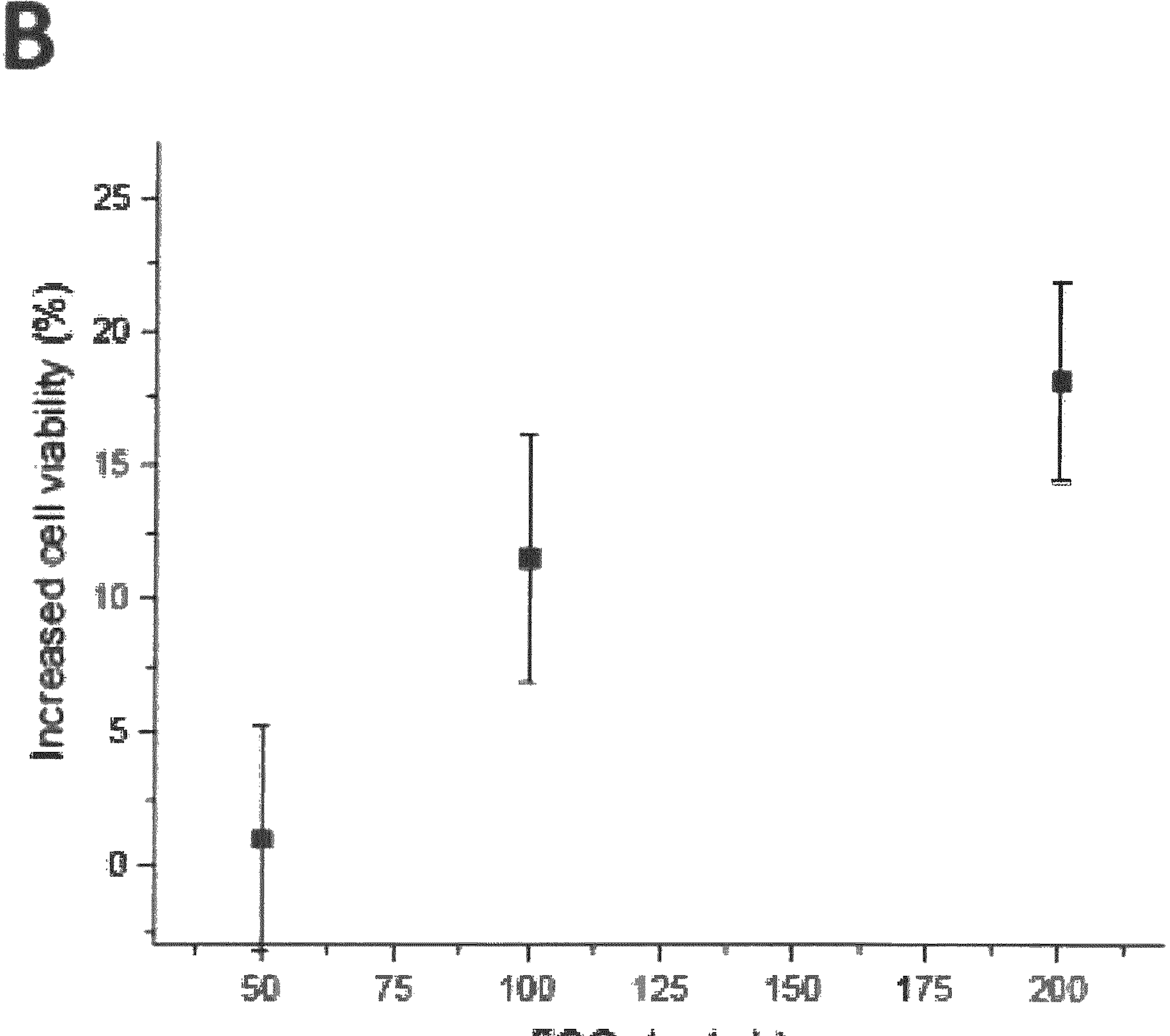

FIG. 4: (A) Polymerization test of the recombinant FGG with FXIII. 0 (control), time above lanes shows reaction duration and increased intensity of FGG-dimer formation at 100 kDa, (B) FGG in cell medium leads to a dose-dependent increase of viability in comparison to a control (cell media alone).

Figure 5:
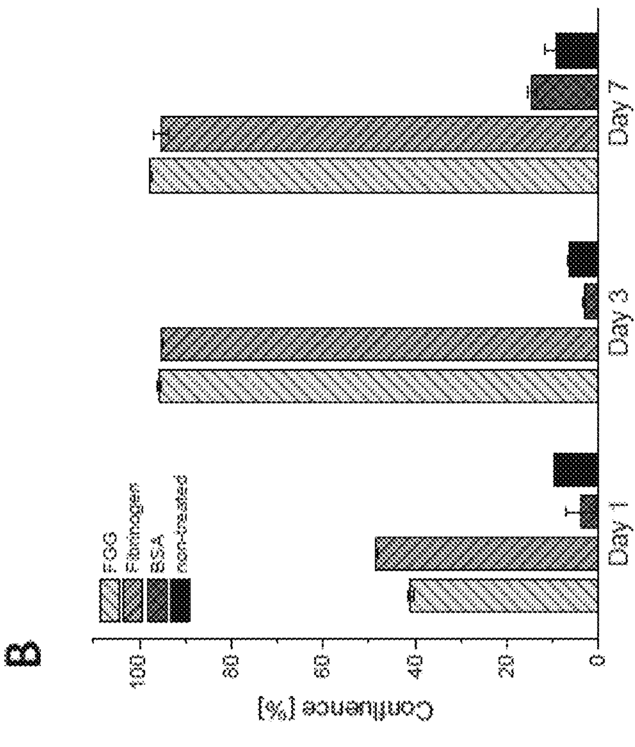
Figure 5:
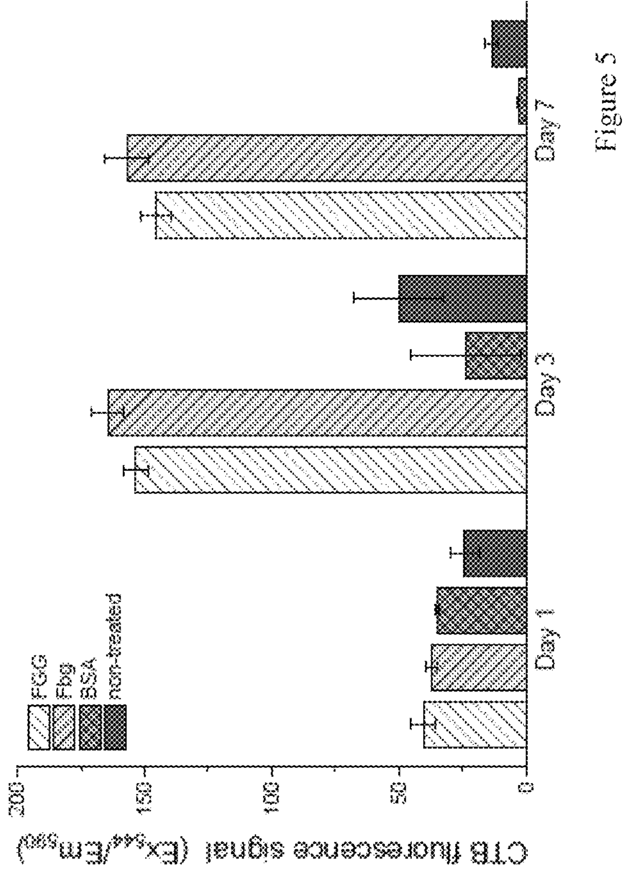

FIG. 5: (A) CTB test showing proliferation of AD-MSCs on different types of cell culture coating during 1, 3 and 7 days of culture; (B) Growth of AD-MSCs on FGG, fibrinogen, BSA and uncoated cell culture wells, shown as confluence determined with Fiji. Cell concentration: 15,000 cells/well; Imaging with Biotek® Cytation 5™ system (4× magnification).

Figure 6:
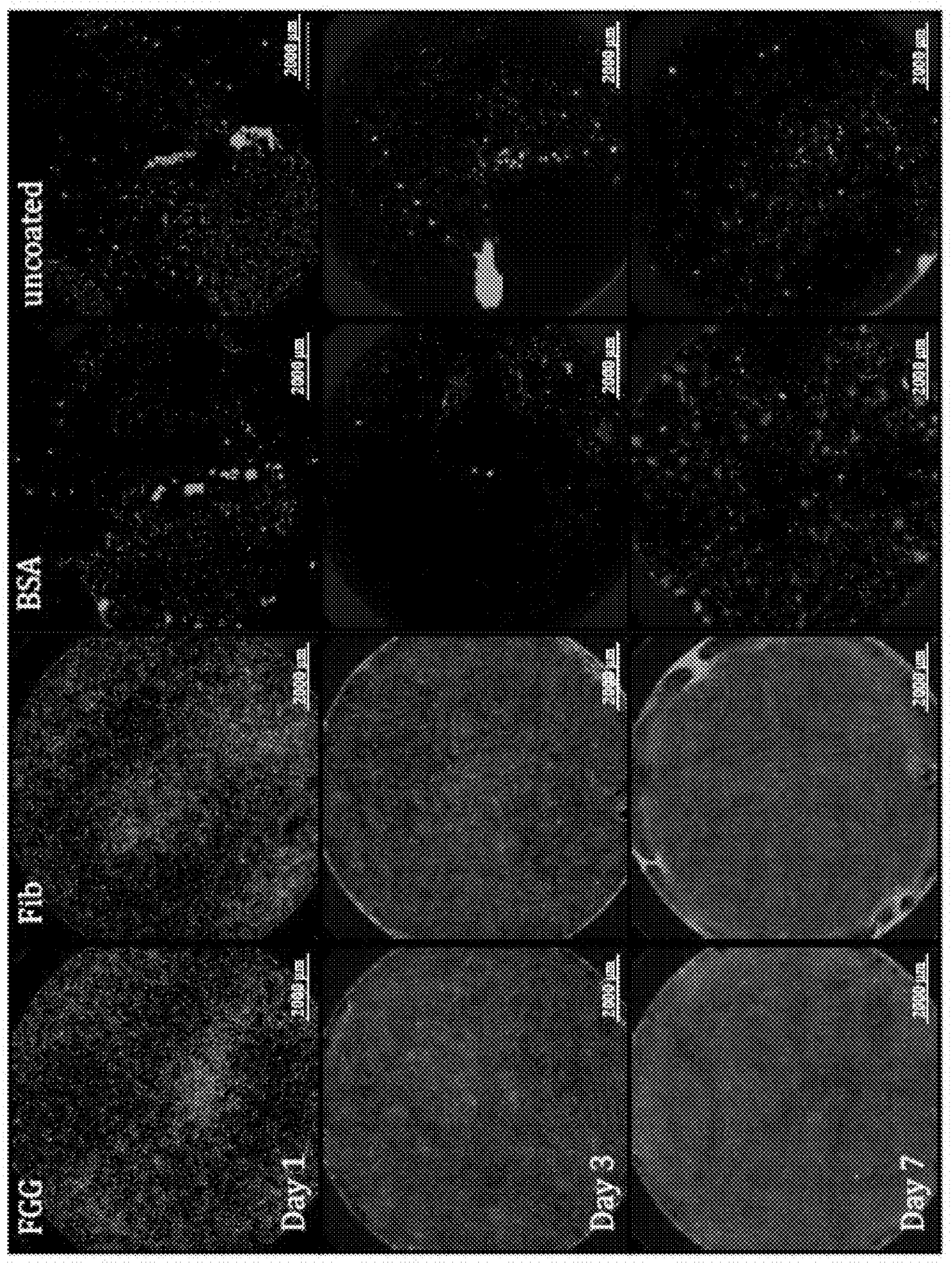

FIG. 6: Growth of AD-MSCs on FGG, fibrinogen, BSA and uncoated cell culture wells after 1, 3 and 7 days of culture, 15,000 cells/well; Fluorescence imaging with Biotek® Cytation 5™ system (4× magnification), Cell staining with Calcein-AM, aggregates form by cells grown on BSA and without coating.

Figure 7:
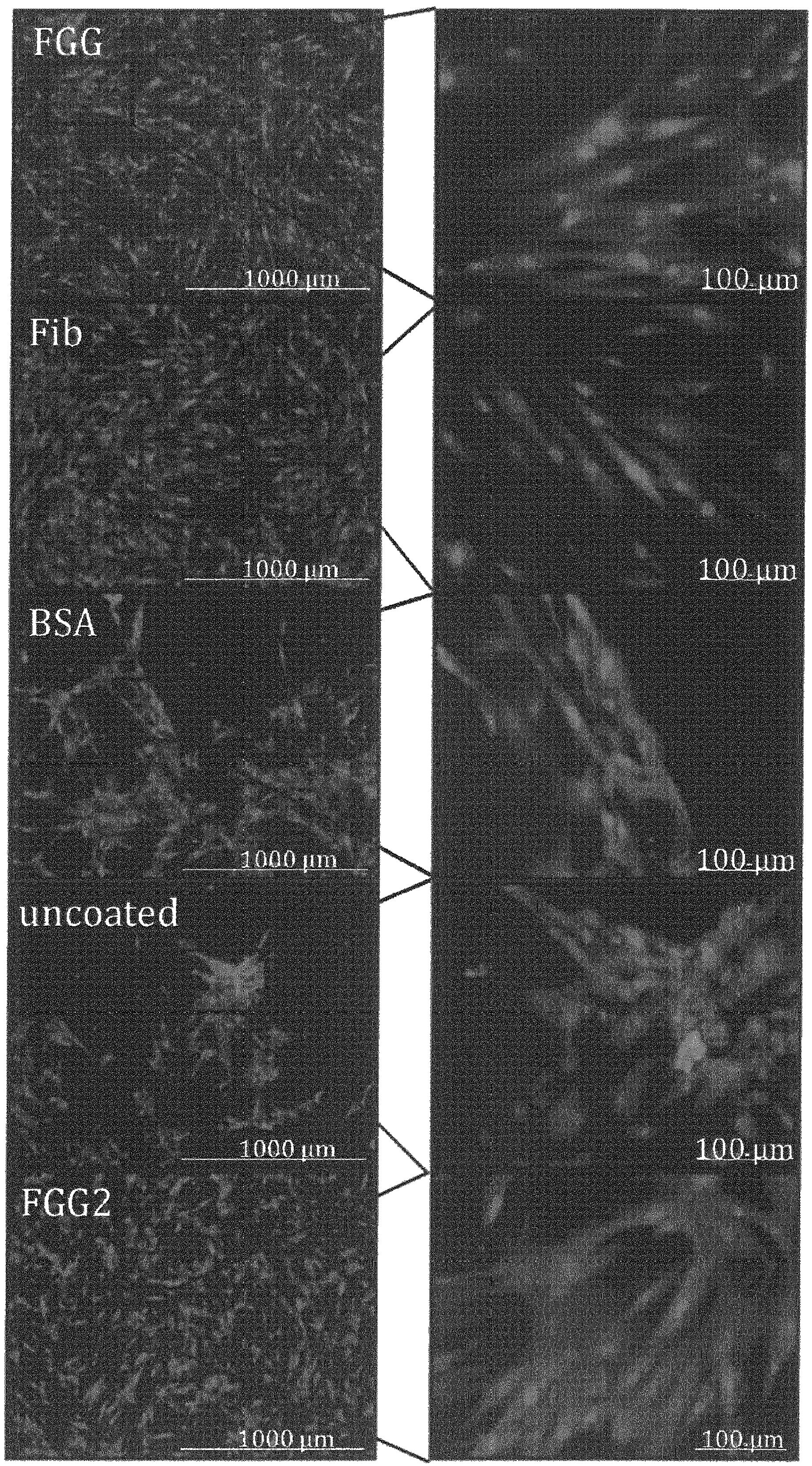

FIG. 7: Cell morphology after 24 h growth of AD-MSCs on FGG, fibrinogen, BSA and uncoated cell culture wells, cell concentration: 15,000 cells/well in 48-well plates; fluorescence imaging with Biotek® Cytation 5™ system (left: 4×, right 20× magnification), live cell imaging (Calcein-AM, green), cell nuclei staining (DAPI, blue), dead cell imaging (propidium iodide, red), FGG is coating of purified soluble protein, FGG2 coating directly from solubilized IBs without purification.

Figure 8:
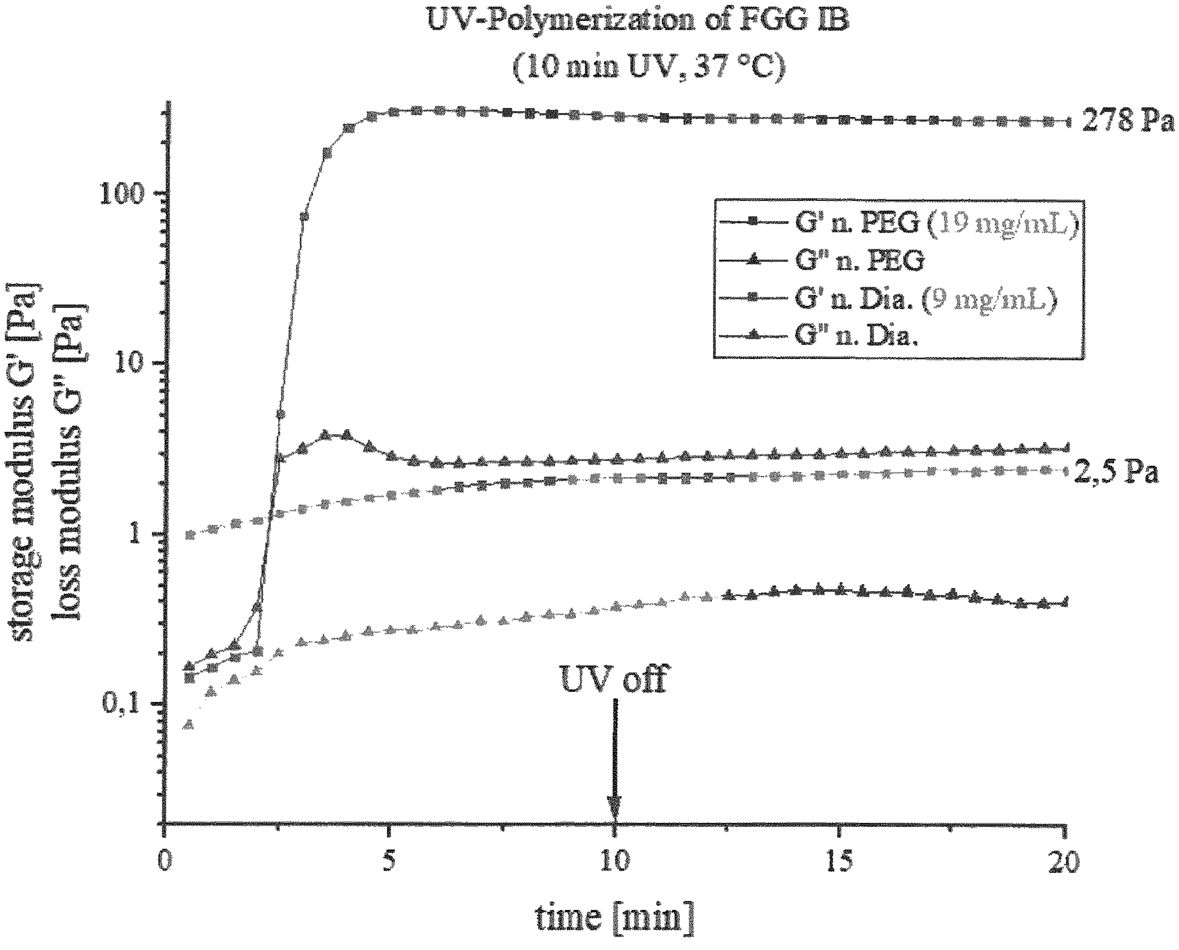

FIG. 8: Time-sweep oscillatory test of FGG-PEGDA (biohybrid biopolymer of FGG modified with photoactive PEG-DA), showing the formation of a strong hydrogel during in situ UV light illumination. Rheology parameters were: 1% amplitude, 1 Hz, 37° C., EGG-PEGDA 19 mg/ml.

The present invention relates the following amino acid and nucleotide sequences:

SEQ ID NO: 1

Fibrinogen gamma chain (FGG)
MYVATRDNCCILDERFGSYCPTTCGIADFLSTYQTKVDKDLQSLEDILHQVENKTSEVKQL
IKAIQLTYNPDESSKPNMIDAATLKSRKMLEEIMKYEASILTHDSSIRYLQEIYNSNNQKI
VNLKEKVAQLEAQCQEPCKDTVQIHDITGKDCQDIANKGAKQSGLYFIKPLKANQQFLVYC
EIDGSGNGWTVFQKRLDGSVDFKKNWIQYKEGFGHLSPTGTTEFWLGNEKIHLISTQSAIP
YALRVELEDWNGRTSTADYAMFKVGPEADKYRLTYAYFAGGDAGDAFDGFDFGDDPSDKFF
TSHNGMQFSTWDNDNDKFEGNCAEQDGSGWWMNKCHAGHLNGVYYQGGTYSKASTPNGYDN
GIIWATWKTRWYSMKKTTMKIIPFNRLTIGEGQQHHLGGAKQAGDV

SEQ ID NO: 2

His-Tag
MGHHHHHHHHHHSSGHIEGRHMLEDI

SEQ ID NO 3

His-Tag-FGG
MGHHHHHHHHHHSSGHIEGRHMLEDIMYVATRDNCCILDERFGSYCPTTCGIADFLSTYQT
KVDKDLQSLEDILHQVENKTSEVKQLIKAIQLTYNPDESSKPNMIDAATLKSRKMLEEIMK
YEASILTHDSSIRYLQEIYNSNNQKIVNLKEKVAQLEAQCQEPCKDTVQIHDITGKDCQDI
ANKGAKQSGLYFIKPLKANQQFLVYCEIDGSGNGWTVFQKRLDGSVDFKKNWIQYKEGFGH
LSPTGTTEFWLGNEKIHLISTQSAIPYALRVELEDWNGRTSTADYAMFKVGPEADKYRLTY
AYFAGGDAGDAFDGFDFGDDPSDKFFTSHNGMQFSTWDNDNDKFEGNCAEQDGSGWWMNKC
HAGHLNGVYYQGGTYSKASTPNGYDNGIIWATWKTRWYSMKKTTMKIIPFNRLTIGEGQQH
HLGGAKQAGDV

SEQ ID NO: 4

FGG coding sequence
ATGTATGTTGCAACCCGTGATAATTGCTGCATTCTGGATGAACGTTTTGGTAGCTATTGTC
CGACCACCTGTGGTATTGCAGATTTTCTGAGCACCTATCAGACCAAAGTTGATAAAGATCT
GCAGAGCCTGGAAGATATTCTGCATCAGGTTGAAAACAAAACCAGCGAAGTTAAACAGCTG
ATTAAAGCAATTCAGCTGACCTATAATCCGGATGAAAGCAGCAAACCGAATATGATTGATG
CAGCAACCCTGAAAAGCCGTAAAATGCTGGAAGAGATCATGAAATATGAAGCCAGCATTCT
GACCCATGATAGCAGCATTCGTTATCTGCAAGAAATCTACAATAGCAATAATCAGAAAATT
GTGAATCTGAAAGAAAAAGTGGCACAGCTGGAAGCACAGTGTCAAGAACCGTGTAAAGATA
CCGTTCAGATTCATGATATCACCGGTAAAGATTGTCAGGATATTGCAAACAAAGGTGCAAA
ACAGAGCGGTCTGTATTTTATCAAACCGCTGAAAGCAAATCAGCAGTTTCTGGTGTATTGC
GAAATTGATGGTAGCGGTAATGGTTGGACCGTTTTTCAGAAACGTCTGGATGGTAGCGTGG
ACTTCAAAAAAAACTGGATTCAGTATAAAGAAGGCTTTGGTCATCTGAGCCCGACCGGCAC
CACCGAATTTTGGCTGGGTAATGAAAAAATTCATCTGATTAGCACCCAGAGCGCAATTCCG
TATGCACTGCGTGTTGAACTGGAAGATTGGAATGGTCGTACCAGCACCGCAGATTATGCAA
TGTTTAAAGTTGGTCCGGAAGCCGATAAATATCGTCTGACCTATGCATATTTTGCCGGTGG
TGATGCCGGTGATGCATTTGATGGTTTTGATTTTGGTGATGATCCGAGCGATAAATTCTTT
ACCAGCCATAATGGTATGCAGTTTAGCACCTGGGATAACGATAACGATAAATTTGAAGGCA
ATTGTGCCGAACAGGATGGTAGTGGTTGGTGGATGAATAAATGTCATGCAGGTCATCTGAA
CGGCGTTTATTATCAGGGTGGCACCTATAGCAAAGCAAGCACCCCGAATGGTTATGATAAT
GGTATTATTTGGGCAACCTGGAAAACCCGTTGGTACAGCATGAAAAAAACCACCATGAAAA
TCATCCCGTTTAACCGTCTGACCATTGGTGAAGGTCAGCAGCATCATCTGGGTGGTGCAAA
ACAAGCCGGTGATGTG

SEQ ID NO: 5

Nucleic acid for FGG expression in *E. coli*
CTCGAGGATATCATGTATGTTGCAACCCGTGATAATTGCTGCATTCTGGATGAACGTTTTG
GTAGCTATTGTCCGACCACCTGTGGTATTGCAGATTTTCTGAGCACCTATCAGACCAAAGT
TGATAAAGATCTGCAGAGCCTGGAAGATATTCTGCATCAGGTTGAAAACAAAACCAGCGAA
GTTAAACAGCTGATTAAAGCAATTCAGCTGACCTATAATCCGGATGAAAGCAGCAAACCGA
ATATGATTGATGCAGCAACCCTGAAAAGCCGTAAAATGCTGGAAGAGATCATGAAATATGA
AGCCAGCATTCTGACCCATGATAGCAGCATTCGTTATCTGCAAGAAATCTACAATAGCAAT
AATCAGAAAATTGTGAATCTGAAAGAAAAAGTGGCACAGCTGGAAGCACAGTGTCAAGAAC
CGTGTAAAGATACCGTTCAGATTCATGATATCACCGGTAAAGATTGTCAGGATATTGCAAA
CAAAGGTGCAAAACAGAGCGGTCTGTATTTTATCAAACCGCTGAAAGCAAATCAGCAGTTT
CTGGTGTATTGCGAAATTGATGGTAGCGGTAATGGTTGGACCGTTTTTCAGAAACGTCTGG
ATGGTAGCGTGGACTTCAAAAAAAACTGGATTCAGTATAAAGAAGGCTTTGGTCATCTGAG
CCCGACCGGCACCACCGAATTTTGGCTGGGTAATGAAAAAATTCATCTGATTAGCACCCAG
AGCGCAATTCCGTATGCACTGCGTGTTGAACTGGAAGATTGGAATGGTCGTACCAGCACCG
CAGATTATGCAATGTTTAAAGTTGGTCCGGAAGCCGATAAATATCGTCTGACCTATGCATA
TTTTGCCGGTGGTGATGCCGGTGATGCATTTGATGGTTTTGATTTTGGTGATGATCCGAGC
GATAAATTCTTTACCAGCCATAATGGTATGCAGTTTAGCACCTGGGATAACGATAACGATA
AATTTGAAGGCAATTGTGCCGAACAGGATGGTAGTGGTTGGTGGATGAATAAATGTCATGC
AGGTCATCTGAACGGCGTTTATTATCAGGGTGGCACCTATAGCAAAGCAAGCACCCCGAAT
GGTTATGATAATGGTATTATTTGGGCAACCTGGAAAACCCGTTGGTACAGCATGAAAAAAA
CCACCATGAAAATCATCCCGTTTAACCGTCTGACCATTGGTGAAGGTCAGCAGCATCATCT
GGGTGGTGCAAAACAAGCCGGTGATGTGTAATAAAAGGATCCGTCGAC

SEQ ID NO: 6

His-Tag-FGG coding sequence
ATGGGCCATCATCATCATCATCATCATCATCATCACAGCAGCGGCCATATCGAAGGTCGTC
ATATGCTCGAGGATATCATGTATGTTGCAACCCGTGATAATTGCTGCATTCTGGATGAACG
TTTTGGTAGCTATTGTCCGACCACCTGTGGTATTGCAGATTTTCTGAGCACCTATCAGACC
AAAGTTGATAAAGATCTGCAGAGCCTGGAAGATATTCTGCATCAGGTTGAAAACAAAACCA
GCGAAGTTAAACAGCTGATTAAAGCAATTCAGCTGACCTATAATCCGGATGAAAGCAGCAA
ACCGAATATGATTGATGCAGCAACCCTGAAAAGCCGTAAAATGCTGGAAGAGATCATGAAA -continued

```
TATGAAGCCAGCATTCTGACCCATGATAGCAGCATTCGTTATCTGCAAGAAATCTACAATA
GCAATAATCAGAAAATTGTGAATCTGAAAGAAAAAGTGGCACAGCTGGAAGCACAGTGTCA
AGAACCGTGTAAAGATACCGTTCAGATTCATGATATCACCGGTAAAGATTGTCAGGATATT
GCAAACAAAGGTGCAAAACAGAGCGGTCTGTATTTTATCAAACCGCTGAAAGCAAATCAGC
AGTTTCTGGTGTATTGCGAAATTGATGGTAGCGGTAATGGTTGGACCGTTTTTCAGAAACG
TCTGGATGGTAGCGTGGACTTCAAAAAAAACTGGATTCAGTATAAAGAAGGCTTTGGTCAT
CTGAGCCCGACCGGCACCACCGAATTTTGGCTGGGTAATGAAAAAATTCATCTGATTAGCA
CCCAGAGCGCAATTCCGTATGCACTGCGTGTTGAACTGGAAGATTGGAATGGTCGTACCAG
CACCGCAGATTATGCAATGTTTAAAGTTGGTCCGGAAGCCGATAAATATCGTCTGACCTAT
GCATATTTTGCCGGTGGTGATGCCGGTGATGCATTTGATGGTTTTGATTTTGGTGATGATC
CGAGCGATAAATTCTTTACCAGCCATAATGGTATGCAGTTTAGCACCTGGGATAACGATAA
CGATAAATTTGAAGGCAATTGTGCCGAACAGGATGGTAGTGGTTGGTGGATGAATAAATGT
CATGCAGGTCATCTGAACGGCGTTTATTATCAGGGTGGCACCTATAGCAAAGCAAGCACCC
CGAATGGTTATGATAATGGTATTATTTGGGCAACCTGGAAAACCCGTTGGTACAGCATGAA
AAAAACCACCATGAAAATCATCCCGTTTAACCGTCTGACCATTGGTGAAGGTCAGCAGCAT
CATCTGGGTGGTGCAAAACAAGCCGGTGATGTGTAATAAAAGGATCCGTCGAC
```

SEQ ID NO: 7

AGDV Binding site
AGDV

SEQ ID NO: 8

Platelet binding site on $FGG_{427-438}$
HHLGGAKQAGDV

SEQ ID NO: 9

Mac-1 or αMβ2 binding site at $FGG_{404-422}$
YSMKKTTMKIIPFNRLTIG

SEQ ID NO: 10

Binding site for integrin αVβ3 at $FGG_{217-229}$
WTVFQKRLDGSV

SEQ ID NO: 11

Binding site for integrin αVβ3 at $FGG_{373-385}$
GVYYQGGTYSKAS

The present invention will be further illustrated by the following example without being limited thereto.

EXAMPLES

Example 1

Design of Construct and Creation of Production Strain Tuner™ (DE3)-FGG

The gene sequence for the recombinant expression of the human γA chain in *Escherichia coli* corresponds to the mature protein (amino acid 27-437, Gene Accession Number C9JCS4; FIG. 1) and was produced by a gene synthesis service (Life Technologies). The expression vector pET-16b (Merck Millipore, USA) was chosen to produce FGG with the expression system *E. coli*. The gene sequence of FGG was cloned in-frame with the sequence for a N-terminal polyhistidine affinity tag (His-tag). Sequencing of the entire fragment in both directions confirmed the integrity of the coding sequence. The confirmed plasmid was used for transformation of competent Tuner™ (DE3) host cells via heat shock transformation, resulting in production strain Tuner™ (DE3)-FGG. The recombinant biopolymer is expressed at 35° C. in the intracellular fraction as inclusion bodies (IBs) after induction with 0.58 mM isopropyl-β-D thiogalactopyranoside (IPTG) (FIG. 2).

Example 2

Production and Purification of FGG

FGG is produced in fed-batch cultivation at the 10 L scale, which can be up- or downscaled according to requirement. Inoculation was performed with Tuner™ (DE3)-FGG precultures in minimal DNB medium containing 50 mg/ml carbenicillin at pH 6.8, which have been cultivated for 10-12 h (OD600=0.1). A stainless steel bench-top bioreactor (Sartorius) equipped with all necessary sensors for process control was used for the main cultivation. The process is performed in minimal DNB medium with 50 mg/ml carbenicillin. The operation parameters were set and controlled at pH 6.8, temperature 35° C., gas supply 4 L*min-1 and dissolved oxygen level of 30% air saturation. After depletion of glucose in the main medium, a glucose feed was started (0.8 g/min). A typical fermentation lasts 18 h, after which medium is removed from the biomass by centrifugation.

Cell pellets were washed, resuspended in lysis buffer (50 mM MOPS, 150 mM NaCl, 1 mM EDTA) and disrupted through multiple passages (8×) in a French press with 9 psi. The resulting mixture was homogenized and centrifuged 10,000×g for 60 ni at 4° C. The pellet containing the IBs was washed and centrifuged multiple times (3×) to remove residual impurities in a buffer of 50 mM Tris HCl, 100 mM NaCl, 1 M urea, 1 mM EDTA and 1% Triton. Typical total yields of the process are 350 g wet weight IBs containing FGG. (70% total FGG protein pro 1 g IB)

The further treatment of FGG depends on its final application. Since the protein doesn't exist in its natural milieu of the complete fibrinogen molecule, it is not expected to possess a "natural" conformation on its own. Its bioactivity is mainly related to its sequence. It was shown that a simple solubilization of FGG in (50 mM Tris-HCl, 150 mM NaCl, 5 M urea, pH 8 frozen overnight, thawed and then centrifuged for 30 min at 15,000×g and 4° C. to remove aggregates) can be used to coat cell culture plates with excellent results (cf. FIG. 7). In addition, the IBs can be used to coat plates directly without solubilization at all. If an application requires soluble FGG protein of high purity (>90%), a two-step process of chromatographic purification was developed, consisting of ion metal affinity chromatography (IMAC) and a size exclusion chromatography (SEC).

Details of Purification Procedure

Solubilized EGG was applied to a HisTrap HP column (GE Healthcare, USA, column volume, CV=5 ml) previously equilibrated with 5 CV equilibration buffer (5 M urea, 50 mM Tris-HCl, 150 mM NaCl, 20 mM imidazol, pH 8) using an ÄKTA Pure system (GE Healthcare, USA). Subsequently, the column was washed with 5 CV equilibration buffer to remove impurities. Elution was done with a buffer containing 5 M urea, 50 mM Tris-HCl, 150 mM NaCl, 200 mM imidazol, pH 8. Flow rates were kept at 5 ml/min. Eluted IMAC fractions (5 ml) were further purified using size exclusion chromatography with a HiLoad Superdex 75 pg (GE Healthcare, USA, CV=120 ml). The SEC column was equilibrated with 2 CV equilibrating buffer (10 mM Tris-HCl). Then sample was applied and eluted from the column with 1.5 CV running buffer (50 mM Tris-HCl, 150 mM NaCl, 2 M urea, pH 8). Flow rate in SEC was kept at 1 ml/min. Typical purities of 55 kDa EGG protein after purification are 64.5% after IMAC and 91.3% after SEC. After SEC, buffer exchange and simultaneous urea removal was performed with Vivaspin®20 (Sartorius, MWCO=kDa) against PBS, pH 7.4. The final FGG product was filtered using 0.22 μm PES sterile filters (Sartorius, Germany) and stored frozen before further application (FIG. 3).

Example 3

Characterization and Application of FGG

One way to characterize the recombinant FGG produced in *E. coli* is to investigate whether its crosslinking sites (Gln398 and Lys406) for Factor XIII are accessible in a manner similar to native fibrinogen. Polymerization of purified, soluble recombinant FGG (170 μg/mL) with factor XIII (0.5 mg/mL, 1.1 U/mL) was initiated with the addition of human α-thrombin (0.1 U/mL). The reactions were run at 37° C. in 50 mmol/L TBS buffer, pH 7.4 and terminated at selected intervals by addition of 1% SDS and 2% 2-mercaptoethanol. Control samples (labeled 0) were prepared by adding SDS and 2-mercaptoethanol to fibrinogen before thrombin and factor XIII. Using SDS-PAGE analysis, it could be demonstrated that recombinant FGG can be crosslinked by factor XIII and produces dimers (about 100 kDa) and higher molecular weight FGG structures after 30 mi (FIG. 4).

The biological activity of the produced FGG was tested in mammalian cell culture. Mammalian cells, like adipose-derived mesenchymal stem cells (AD-MSCs) used in this experiment, need to be able to adhere to an extracellular matrix for growth, communication and other intercellular interactions. The recombinant FGG, as well as human fibrinogen and BSA were used to coat cell culture plates. Uncoated plates were employed as a control. All proteins were coated in the same concentration (500 μg/ml).

MSCs were cultured on the various coatings and adhesion, confluence, morphology and viability of the cells was examined. It could be shown that viability (determined indirectly as proliferation with the CTB assay) was highest on the FGG and fibrinogen coatings. Moreover, FGG enhanced cell proliferation in a dose-dependent manner (FIG. 5). Cells growing on FGG and fibrinogen displayed higher confluence, while cells on integrin-free BSA or without coating developed aggregates (FIG. 6). In addition, an examination of cell morphology displayed spindle-like shape and morphology for AD-MSCs growing on FGG and fibrinogen (FIG. 7). The recombinant FGG was indistinguishable in performance to native fibrinogen in mammalian cell culture. Results were confirmed for other cell types as well (data not shown).

Details of Cell Culture

Shown cell experiments were performed with a culture of human adipose-derived mesenchymal stem cells (hAD-MSC). Cells were expanded in α-MEM medium (1 g L-1 glucose, 10% human serum, 2 mM L-glutamine and 50 μg mL-1 gentamicin) and were harvested by accutase treatment. Experiments were performed with hAD-MSCs of passages two to eight.

Example 4

Modification of FGG Biopolymer

Although it has been shown that FGG can be crosslinked by factor XIII as natural fibrinogen (FIG. 4), this doesn't provide sufficient stability for the generation of a 3D network. To crosslink FGG with the aim to create a hydrogel for 3D cell encapsulation, for example, additional modifications are required. Crosslinking can be achieved by chemical modification with a synthetic polymer, for example PEG. Another strategy is to use the synthetic moiety to create a biohybrid material with a tunable property. For example, modification with PEG diacrylate (PEG-DA) provided a FGG-photoactive material, which can be used for e.g. bioprinting, stereolithography, and 3D cell culture. Modification with polymers like Pluronic F127 provide a EGG-temperature switch, which can be used for cell delivery or, in the area of cell culture applications, for the creation of responsive sheets for enzyme-free cell detachment. In all cases, FGG provides the biological activity of the biohybrid material, while the synthetic polymer contributes to the desired physicochemical property. The aim of modification with synthetic moieties (modified biohybrid material) is (i) introducing crosslinking or design/control of mechanical properties (PEG) or (ii) addition of "tunable" properties like temperature switch (e.g. Pluronic F127) or light polymerization (e. g. PEG-DA) (FIG. 8).

The invention claimed is:

1. An isolated, recombinant polypeptide, comprising
(i) the gamma chain of fibrinogen, and
(ii) a His-Tag;
wherein said polypeptide comprises
(a) the amino acid sequence according to SEQ ID NO:3, or
(b) an amino acid sequence having at least 95% sequence identity to SEQ ID NO: 3 and having fibrinogen gamma chain activity and His-Tag functionality;
wherein fibrinogen gamma chain activity refers to the characteristic of having functional binding sites for integrins, leukocytes, platelets, fibroblasts, endothelial cells and/or fibroblast growth factor 2 (FGF-2).

2. The isolated, recombinant polypeptide according to claim 1, wherein said gamma chain of fibrinogen comprises binding sites for integrins, leukocytes, platelets, fibroblasts, endothelial cells and/or fibroblast growth factor 2 (FGF-2).

3. The isolated, recombinant polypeptide according to claim 1, wherein said gamma chain of fibrinogen comprises
(i) the amino acid sequence according to SEQ ID NO: 1, or
(ii) an amino acid sequence having at least 95% sequence identity to SEQ ID NO: 1 and having fibrinogen gamma chain activity.

4. The isolated, recombinant polypeptide according to claim 1, wherein said His-Tag comprises
(i) the amino acid sequence according to SEQ ID NO: 2, or
(ii) an amino acid sequence having at least 95% sequence identity to SEQ ID NO: 2 and having His-Tag functionality.

5. A biohybrid material, comprising a conjugate comprising the polypeptide according to claim 1 and one or more moieties, selected from the group consisting of polyethylene glycol (PEG), PEG derivatives, PEG diacrylate (PEG-DA), poly(oligo (ethylene glycol) methyl ether methacrylate (POEGMA), poly(N-(2-hydroxypropyl)-methacrylamide) (PHPMA) and HPMA copolymers, poly(vinylpyrrolidone) (PVP), poly(ethyleneimine) (PEI), poly(acroloylmorpholine) (PAcM), poly(2-ethyl 2-oxazoline) (PEOZ), divinylethermaleic anhydride/acid copolymer (DIVEMA), poly(styrene-co-maleic acid/anhydride) (SMA), poly(vinyl alcohol) (PVA) and temperature-sensitive polymers including poloxamers, poly(N-isopropylacrylamide) (PNIPAM), poly(N,N-diethylacrylamide) (PDEAM), poly(methylvinylether) (PMVE), poly(N-vinylcaprolactam) (PNVC1), and mixtures thereof.

6. The isolated, recombinant polypeptide according to claim 1, wherein said polypeptide comprises the amino acid sequence according to SEQ ID NO:3.

7. The isolated, recombinant polypeptide according to claim 1, wherein said polypeptide comprises an amino acid sequence having at least 95% sequence identity to SEQ ID NO:3 and having fibrinogen gamma chain activity and His-Tag functionality.

8. The isolated, recombinant polypeptide according to claim 3, wherein said gamma chain of fibrinogen comprises the amino acid sequence according to SEQ ID NO: 1.

9. The isolated, recombinant polypeptide according to claim 3, wherein said gamma chain of fibrinogen comprises an amino acid sequence having at least 95% sequence identity to SEQ ID NO: 1 and having fibrinogen gamma chain activity.

10. The isolated, recombinant polypeptide according to claim 4, wherein said His-Tag comprises the amino acid sequence according to SEQ ID NO: 2.

11. The isolated, recombinant polypeptide according to claim 4, wherein said His-Tag comprises an amino acid sequence having at least 95% sequence identity to SEQ ID NO: 2 and having His-Tag functionality.

12. The isolated, recombinant polypeptide according to claim 7, wherein said polypeptide comprises an amino acid sequence having at least 96% sequence identity to SEQ ID NO:3 and having fibrinogen gamma chain activity and His-Tag functionality.

13. The isolated, recombinant polypeptide according to claim 12, wherein said polypeptide comprises an amino acid sequence having at least 97% sequence identity to SEQ ID NO:3 and having fibrinogen gamma chain activity and His-Tag functionality.

14. The isolated, recombinant polypeptide according to claim 13, wherein said polypeptide comprises an amino acid sequence having at least 98% sequence identity to SEQ ID NO:3 and having fibrinogen gamma chain activity and His-Tag functionality.

15. The isolated, recombinant polypeptide according to claim 14, wherein said polypeptide comprises an amino acid sequence having at least 99% sequence identity to SEQ ID NO:3 and having fibrinogen gamma chain activity and His-Tag functionality.

* * * * *

SEQUENCE LISTING

```
<160> NUMBER OF SEQ ID NOS: 11

<210> SEQ ID NO 1
<211> LENGTH: 412
<212> TYPE: PRT
<213> ORGANISM: Artificial sequence
<220> FEATURE:
<223> OTHER INFORMATION: Fibrinogen gamma chain (FGG)

<400> SEQUENCE: 1

Met Tyr Val Ala Thr Arg Asp Asn Cys Cys Ile Leu Asp Glu Arg Phe
```

-continued

```
1               5                   10                  15

Gly Ser Tyr Cys Pro Thr Thr Cys Gly Ile Ala Asp Phe Leu Ser Thr
            20                  25                  30

Tyr Gln Thr Lys Val Asp Lys Asp Leu Gln Ser Leu Glu Asp Ile Leu
        35                  40                  45

His Gln Val Glu Asn Lys Thr Ser Glu Val Lys Gln Leu Ile Lys Ala
    50                  55                  60

Ile Gln Leu Thr Tyr Asn Pro Asp Glu Ser Ser Lys Pro Asn Met Ile
65                  70                  75                  80

Asp Ala Ala Thr Leu Lys Ser Arg Lys Met Leu Glu Glu Ile Met Lys
                85                  90                  95

Tyr Glu Ala Ser Ile Leu Thr His Asp Ser Ser Ile Arg Tyr Leu Gln
            100                 105                 110

Glu Ile Tyr Asn Ser Asn Asn Gln Lys Ile Val Asn Leu Lys Glu Lys
        115                 120                 125

Val Ala Gln Leu Glu Ala Gln Cys Gln Glu Pro Cys Lys Asp Thr Val
    130                 135                 140

Gln Ile His Asp Ile Thr Gly Lys Asp Cys Gln Asp Ile Ala Asn Lys
145                 150                 155                 160

Gly Ala Lys Gln Ser Gly Leu Tyr Phe Ile Lys Pro Leu Lys Ala Asn
                165                 170                 175

Gln Gln Phe Leu Val Tyr Cys Glu Ile Asp Gly Ser Gly Asn Gly Trp
            180                 185                 190

Thr Val Phe Gln Lys Arg Leu Asp Gly Ser Val Asp Phe Lys Lys Asn
        195                 200                 205

Trp Ile Gln Tyr Lys Glu Gly Phe Gly His Leu Ser Pro Thr Gly Thr
    210                 215                 220

Thr Glu Phe Trp Leu Gly Asn Glu Lys Ile His Leu Ile Ser Thr Gln
225                 230                 235                 240

Ser Ala Ile Pro Tyr Ala Leu Arg Val Glu Leu Glu Asp Trp Asn Gly
                245                 250                 255

Arg Thr Ser Thr Ala Asp Tyr Ala Met Phe Lys Val Gly Pro Glu Ala
            260                 265                 270

Asp Lys Tyr Arg Leu Thr Tyr Ala Tyr Phe Ala Gly Gly Asp Ala Gly
        275                 280                 285

Asp Ala Phe Asp Gly Phe Asp Phe Gly Asp Asp Pro Ser Asp Lys Phe
    290                 295                 300

Phe Thr Ser His Asn Gly Met Gln Phe Ser Thr Trp Asp Asn Asp Asn
305                 310                 315                 320

Asp Lys Phe Glu Gly Asn Cys Ala Glu Gln Asp Gly Ser Gly Trp Trp
                325                 330                 335

Met Asn Lys Cys His Ala Gly His Leu Asn Gly Val Tyr Tyr Gln Gly
            340                 345                 350

Gly Thr Tyr Ser Lys Ala Ser Thr Pro Asn Gly Tyr Asp Asn Gly Ile
        355                 360                 365

Ile Trp Ala Thr Trp Lys Thr Arg Trp Tyr Ser Met Lys Lys Thr Thr
    370                 375                 380

Met Lys Ile Ile Pro Phe Asn Arg Leu Thr Ile Gly Glu Gly Gln Gln
385                 390                 395                 400

His His Leu Gly Gly Ala Lys Gln Ala Gly Asp Val
                405                 410
```

<210> SEQ ID NO 2

```
<211> LENGTH: 26
<212> TYPE: PRT
<213> ORGANISM: Artificial sequence
<220> FEATURE:
<223> OTHER INFORMATION: His-Tag

<400> SEQUENCE: 2

Met Gly His His His His His His His His His His Ser Ser Gly His
1               5                   10                  15

Ile Glu Gly Arg His Met Leu Glu Asp Ile
            20                  25


<210> SEQ ID NO 3
<211> LENGTH: 438
<212> TYPE: PRT
<213> ORGANISM: Artificial sequence
<220> FEATURE:
<223> OTHER INFORMATION: His-Tag-FGG

<400> SEQUENCE: 3

Met Gly His His His His His His His His His His Ser Ser Gly His
1               5                   10                  15

Ile Glu Gly Arg His Met Leu Glu Asp Ile Met Tyr Val Ala Thr Arg
            20                  25                  30

Asp Asn Cys Cys Ile Leu Asp Glu Arg Phe Gly Ser Tyr Cys Pro Thr
        35                  40                  45

Thr Cys Gly Ile Ala Asp Phe Leu Ser Thr Tyr Gln Thr Lys Val Asp
    50                  55                  60

Lys Asp Leu Gln Ser Leu Glu Asp Ile Leu His Gln Val Glu Asn Lys
65                  70                  75                  80

Thr Ser Glu Val Lys Gln Leu Ile Lys Ala Ile Gln Leu Thr Tyr Asn
                85                  90                  95

Pro Asp Glu Ser Ser Lys Pro Asn Met Ile Asp Ala Ala Thr Leu Lys
            100                 105                 110

Ser Arg Lys Met Leu Glu Glu Ile Met Lys Tyr Glu Ala Ser Ile Leu
        115                 120                 125

Thr His Asp Ser Ser Ile Arg Tyr Leu Gln Glu Ile Tyr Asn Ser Asn
    130                 135                 140

Asn Gln Lys Ile Val Asn Leu Lys Glu Lys Val Ala Gln Leu Glu Ala
145                 150                 155                 160

Gln Cys Gln Glu Pro Cys Lys Asp Thr Val Gln Ile His Asp Ile Thr
                165                 170                 175

Gly Lys Asp Cys Gln Asp Ile Ala Asn Lys Gly Ala Lys Gln Ser Gly
            180                 185                 190

Leu Tyr Phe Ile Lys Pro Leu Lys Ala Asn Gln Gln Phe Leu Val Tyr
        195                 200                 205

Cys Glu Ile Asp Gly Ser Gly Asn Gly Trp Thr Val Phe Gln Lys Arg
    210                 215                 220

Leu Asp Gly Ser Val Asp Phe Lys Lys Asn Trp Ile Gln Tyr Lys Glu
225                 230                 235                 240

Gly Phe Gly His Leu Ser Pro Thr Gly Thr Thr Glu Phe Trp Leu Gly
                245                 250                 255

Asn Glu Lys Ile His Leu Ile Ser Thr Gln Ser Ala Ile Pro Tyr Ala
            260                 265                 270

Leu Arg Val Glu Leu Glu Asp Trp Asn Gly Arg Thr Ser Thr Ala Asp
        275                 280                 285

Tyr Ala Met Phe Lys Val Gly Pro Glu Ala Asp Lys Tyr Arg Leu Thr
```

```
    290                 295                 300

Tyr Ala Tyr Phe Ala Gly Gly Asp Ala Gly Asp Ala Phe Asp Gly Phe
305                 310                 315                 320

Asp Phe Gly Asp Asp Pro Ser Asp Lys Phe Phe Thr Ser His Asn Gly
                325                 330                 335

Met Gln Phe Ser Thr Trp Asp Asn Asp Asn Asp Lys Phe Glu Gly Asn
            340                 345                 350

Cys Ala Glu Gln Asp Gly Ser Gly Trp Trp Met Asn Lys Cys His Ala
        355                 360                 365

Gly His Leu Asn Gly Val Tyr Tyr Gln Gly Gly Thr Tyr Ser Lys Ala
    370                 375                 380

Ser Thr Pro Asn Gly Tyr Asp Asn Gly Ile Ile Trp Ala Thr Trp Lys
385                 390                 395                 400

Thr Arg Trp Tyr Ser Met Lys Lys Thr Thr Met Lys Ile Ile Pro Phe
                405                 410                 415

Asn Arg Leu Thr Ile Gly Glu Gly Gln Gln His His Leu Gly Gly Ala
            420                 425                 430

Lys Gln Ala Gly Asp Val
        435


<210> SEQ ID NO 4
<211> LENGTH: 1236
<212> TYPE: DNA
<213> ORGANISM: Artificial sequence
<220> FEATURE:
<223> OTHER INFORMATION: FGG coding sequence

<400> SEQUENCE: 4

atgtatgttg caacccgtga taattgctgc attctggatg aacgttttgg tagctattgt     60

ccgaccacct gtggtattgc agattttctg agcacctatc agaccaaagt tgataaagat    120

ctgcagagcc tggaagatat tctgcatcag gttgaaaaca aaaccagcga agttaaacag    180

ctgattaaag caattcagct gacctataat ccggatgaaa gcagcaaacc gaatatgatt    240

gatgcagcaa ccctgaaaag ccgtaaaatg ctggaagaga tcatgaaata tgaagccagc    300

attctgaccc atgatagcag cattcgttat ctgcaagaaa tctacaatag caataatcag    360

aaaattgtga atctgaaaga aaaagtggca cagctggaag cacagtgtca agaaccgtgt    420

aaagataccg ttcagattca tgatatcacc ggtaaagatt gtcaggatat tgcaaacaaa    480

ggtgcaaaac agagcggtct gtattttatc aaaccgctga aagcaaatca gcagtttctg    540

gtgtattgcg aaattgatgg tagcggtaat ggttggaccg tttttcagaa acgtctggat    600

ggtagcgtgg acttcaaaaa aaactggatt cagtataaag aaggctttgg tcatctgagc    660

ccgaccggca ccaccgaatt ttggctgggt aatgaaaaaa ttcatctgat tagcacccag    720

agcgcaattc cgtatgcact gcgtgttgaa ctggaagatt ggaatggtcg taccagcacc    780

gcagattatg caatgtttaa agttggtccg gaagccgata aatatcgtct gacctatgca    840

tattttgccg gtggtgatgc cggtgatgca tttgatggtt ttgattttgg tgatgatccg    900

agcgataaat tctttaccag ccataatggt atgcagttta gcacctggga taacgataac    960

gataaatttg aaggcaattg tgccgaacag gatggtagtg gttggtggat gaataaatgt   1020

catgcaggtc atctgaacgg cgtttattat cagggtggca cctatagcaa agcaagcacc   1080

ccgaatggtt atgataatgg tattatttgg gcaacctgga aaacccgttg gtacagcatg   1140

aaaaaaacca ccatgaaaat catcccgttt aaccgtctga ccattggtga aggtcagcag   1200
```

catcatctgg gtggtgcaaa acaagccggt gatgtg 1236

<210> SEQ ID NO 5
<211> LENGTH: 1268
<212> TYPE: DNA
<213> ORGANISM: Artificial sequence
<220> FEATURE:
<223> OTHER INFORMATION: Nucleic acid for FGG expression in E. coli

<400> SEQUENCE: 5
ctcgaggata tcatgtatgt tgcaacccgt gataattgct gcattctgga tgaacgtttt 60
ggtagctatt gtccgaccac ctgtggtatt gcagattttc tgagcaccta tcagaccaaa 120
gttgataaag atctgcagag cctggaagat attctgcatc aggttgaaaa caaaaccagc 180
gaagttaaac agctgattaa agcaattcag ctgacctata atccggatga aagcagcaaa 240
ccgaatatga ttgatgcagc aaccctgaaa agccgtaaaa tgctggaaga gatcatgaaa 300
tatgaagcca gcattctgac ccatgatagc agcattcgtt atctgcaaga aatctacaat 360
agcaataatc agaaaattgt gaatctgaaa gaaaaagtgg cacagctgga agcacagtgt 420
caagaaccgt gtaaagatac cgttcagatt catgatatca ccggtaaaga ttgtcaggat 480
attgcaaaca aaggtgcaaa acagagcggt ctgtatttta tcaaaccgct gaaagcaaat 540
cagcagtttc tggtgtattg cgaaattgat ggtagcggta atggttggac cgtttttcag 600
aaacgtctgg atggtagcgt ggacttcaaa aaaaactgga ttcagtataa agaaggcttt 660
ggtcatctga gcccgaccgg caccaccgaa ttttggctgg gtaatgaaaa aattcatctg 720
attagcaccc agagcgcaat tccgtatgca ctgcgtgttg aactggaaga ttggaatggt 780
cgtaccagca ccgcagatta tgcaatgttt aaagttggtc cggaagccga taaatatcgt 840
ctgacctatg catattttgc cggtggtgat gccggtgatg catttgatgg ttttgatttt 900
ggtgatgatc cgagcgataa attctttacc agccataatg gtatgcagtt tagcacctgg 960
gataacgata acgataaatt tgaaggcaat tgtgccgaac aggatggtag tggttggtgg 1020
atgaataaat gtcatgcagg tcatctgaac ggcgtttatt atcagggtgg cacctatagc 1080
aaagcaagca ccccgaatgg ttatgataat ggtattattt gggcaacctg gaaaacccgt 1140
tggtacagca tgaaaaaaac caccatgaaa atcatcccgt ttaaccgtct gaccattggt 1200
gaaggtcagc agcatcatct gggtggtgca aaacaagccg gtgatgtgta ataaaaggat 1260
ccgtcgac 1268

<210> SEQ ID NO 6
<211> LENGTH: 1334
<212> TYPE: DNA
<213> ORGANISM: Artificial Sequence
<220> FEATURE:
<223> OTHER INFORMATION: His-Tag-FGG coding sequence

<400> SEQUENCE: 6
atgggccatc atcatcatca tcatcatcat catcacagca gcggccatat cgaaggtcgt 60
catatgctcg aggatatcat gtatgttgca acccgtgata attgctgcat tctggatgaa 120
cgttttggta gctattgtcc gaccacctgt ggtattgcag attttctgag cacctatcag 180
accaaagttg ataaagatct gcagagcctg gaagatattc tgcatcaggt tgaaaacaaa 240
accagcgaag ttaaacagct gattaaagca attcagctga cctataatcc ggatgaaagc 300
agcaaaccga atatgattga tgcagcaacc ctgaaaagcc gtaaaatgct ggaagagatc 360
atgaaatatg aagccagcat tctgacccat gatagcagca ttcgttatct gcaagaaatc 420

```
tacaatagca ataatcagaa aattgtgaat ctgaaagaaa aagtggcaca gctggaagca    480

cagtgtcaag aaccgtgtaa agataccgtt cagattcatg atatcaccgg taaagattgt    540

caggatattg caaacaaagg tgcaaaacag agcggtctgt attttatcaa accgctgaaa    600

gcaaatcagc agtttctggt gtattgcgaa attgatggta gcggtaatgg ttggaccgtt    660

tttcagaaac gtctggatgg tagcgtggac ttcaaaaaaa actggattca gtataaagaa    720

ggctttggtc atctgagccc gaccggcacc accgaatttt ggctgggtaa tgaaaaaatt    780

catctgatta gcacccagag cgcaattccg tatgcactgc gtgttgaact ggaagattgg    840

aatggtcgta ccagcaccgc agattatgca atgtttaaag ttggtccgga agccgataaa    900

tatcgtctga cctatgcata ttttgccggt ggtgatgccg gtgatgcatt tgatggtttt    960

gattttggtg atgatccgag cgataaattc tttaccagcc ataatggtat gcagtttagc   1020

acctgggata acgataacga taaatttgaa ggcaattgtg ccgaacagga tggtagtggt   1080

tggtggatga ataaatgtca tgcaggtcat ctgaacggcg tttattatca gggtggcacc   1140

tatagcaaag caagcacccc gaatggttat gataatggta ttatttgggc aacctggaaa   1200

acccgttggt acagcatgaa aaaaaccacc atgaaaatca tcccgtttaa ccgtctgacc   1260

attggtgaag gtcagcagca tcatctgggt ggtgcaaaac aagccggtga tgtgtaataa   1320

aaggatccgt cgac                                                     1334
```

<210> SEQ ID NO 7
<211> LENGTH: 4
<212> TYPE: PRT
<213> ORGANISM: Artificial sequence
<220> FEATURE:
<223> OTHER INFORMATION: Binding site

<400> SEQUENCE: 7

```
Ala Gly Asp Val
1
```

<210> SEQ ID NO 8
<211> LENGTH: 12
<212> TYPE: PRT
<213> ORGANISM: Artificial Sequence
<220> FEATURE:
<223> OTHER INFORMATION: Binding site on FGG

<400> SEQUENCE: 8

```
His His Leu Gly Gly Ala Lys Gln Ala Gly Asp Val
1               5                   10
```

<210> SEQ ID NO 9
<211> LENGTH: 19
<212> TYPE: PRT
<213> ORGANISM: Artificial Sequence
<220> FEATURE:
<223> OTHER INFORMATION: Binding site on FGG

<400> SEQUENCE: 9

```
Tyr Ser Met Lys Lys Thr Thr Met Lys Ile Ile Pro Phe Asn Arg Leu
1               5                   10                  15

Thr Ile Gly
```

<210> SEQ ID NO 10
<211> LENGTH: 12
<212> TYPE: PRT
<213> ORGANISM: Artificial Sequence -continued

```
<220> FEATURE:
<223> OTHER INFORMATION: Binding site on FGG

<400> SEQUENCE: 10

Trp Thr Val Phe Gln Lys Arg Leu Asp Gly Ser Val
1               5                   10


<210> SEQ ID NO 11
<211> LENGTH: 13
<212> TYPE: PRT
<213> ORGANISM: Artificial Sequence
<220> FEATURE:
<223> OTHER INFORMATION: Binding site on FGG

<400> SEQUENCE: 11

Gly Val Tyr Tyr Gln Gly Gly Thr Tyr Ser Lys Ala Ser
1               5                   10
```